United States Patent
Lira et al.

(10) Patent No.: US 10,253,323 B2
(45) Date of Patent: Apr. 9, 2019

(54) CHLOROPLAST TRANSIT PEPTIDES

(71) Applicant: Dow AgroSciences LLC, Indianapolis, IN (US)

(72) Inventors: Justin M. Lira, Zionsville, IN (US); Robert Cicchillo, Westfield, IN (US); Carla N. Yerkes, Crawfordsville, IN (US); Andrew E. Robinson, Calvert City, KY (US)

(73) Assignee: Dow AgroSciences LLC, Indianapolis, IN (US)

( * ) Notice: Subject to any disclaimer, the term of this patent is extended or adjusted under 35 U.S.C. 154(b) by 81 days.

(21) Appl. No.: 15/239,354

(22) Filed: Aug. 17, 2016

(65) Prior Publication Data

US 2017/0051297 A1 Feb. 23, 2017

Related U.S. Application Data

(60) Provisional application No. 62/207,685, filed on Aug. 20, 2015.

(51) Int. Cl.
*C12N 15/82* (2006.01)
*C07K 14/415* (2006.01)
*C07K 14/325* (2006.01)
*C12N 9/10* (2006.01)

(52) U.S. Cl.
CPC ........ *C12N 15/8221* (2013.01); *C07K 14/325* (2013.01); *C07K 14/415* (2013.01); *C12N 9/1092* (2013.01); *C12N 15/8275* (2013.01); *C12N 15/8277* (2013.01); *C12N 15/8286* (2013.01); *C12Y 205/01019* (2013.01); *C07K 2319/00* (2013.01); *C07K 2319/55* (2013.01); *C07K 2319/60* (2013.01); *Y02A 40/162* (2018.01)

(58) Field of Classification Search
None
See application file for complete search history.

(56) References Cited

U.S. PATENT DOCUMENTS 6,225,114 B1 * 5/2001 Eichholtz ............. C12N 9/1092 435/320.1
8,426,204 B2 * 4/2013 Hammer ............ C12N 15/8214 435/418

OTHER PUBLICATIONS

Bendtsen et al., J Mol Biol 340:783-95 (2004).*
Peterson et al., Nat Meth 8(10):785-86 (2011).*
Savojardo et al., Bioinform 1-7 (2018).*
Bedbrook et al., Nature 287:692-97, 693 (1980).*
Schmidt & Mishkind, Ann Rev Biochem 55:879-912, 881 (1986).*

* cited by examiner

*Primary Examiner* — Russell T Boggs

(57) ABSTRACT

This disclosure concerns compositions and methods for targeting peptides, polypeptides, and proteins to plastids of plastid-containing cells. In some embodiments, the disclosure concerns chloroplast transit peptides that may direct a polypeptide to a plastid, and nucleic acid molecules encoding the same. In some embodiments, the disclosure concerns methods for producing a transgenic plant material (e.g., a transgenic plant) comprising a chloroplast transit peptide, as well as plant materials produced by such methods, and plant commodity products produced therefrom.

46 Claims, 13 Drawing Sheets
Specification includes a Sequence Listing.

Fig. 1

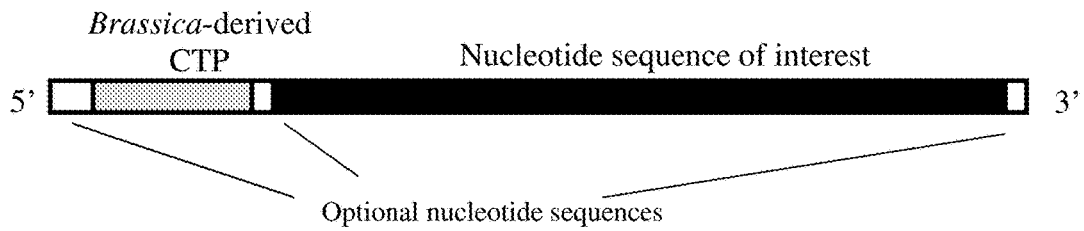

Fig. 2

```
          Dunaliella salina SEQ ID NO:26    (1)  M   RQGGSLP  S  CNAGL  RRVEVGALVVP
               Oryza sativa SEQ ID NO:24    (1)  -----MAATM  S  AAAAA  VSLDQAVAAS
                 Amaranthus SEQ IDNO:25     (1)  -   ATT  N     TGQLHH  LPKTQLPKS
     Chlamydamonas reinhardtii SEQ ID NO:23 (1)  ---M  LLNQR     LGRSS  KNQQVAPLA
                  Calystegia SEQ ID NO:22   (1)  -   VNN  M   RLSPSNL  KPQTPLPSH
                 Glycine max SEQ ID NO:21   (1)  -   VSR  H  LA  STQIF  HS-SNSNKLK
                Brassica napus SEQ ID NO:20 (1)  -   SSR  CH     NPCVII  NLSKSNQNK Dunaliella salina SEQ ID NO:26    (31) RPIS*VND  VPHVY  APLSVARRSCSKS  IR
               Oryza sativa SEQ ID NO:24    (26) AF  S*RKQ  RLPAA  RGG  RVRVRARGRREA
                 Amaranthus SEQ IDNO:25     (30) *K*TLNFG---SNLRI  PKF  SLTNKRVGGQSS
     Chlamydamonas reinhardtii SEQ ID NO:23 (29) RP  S  L*S  SASSV  PAPACS---APAG  GR
                  Calystegia SEQ ID NO:22   (30) LLLG  NS  KN*SSV  VKFFKTGKDSIFT  AR
                 Glycine max SEQ ID NO:21   (29) VN  V  L*RPRLWGA  KSP  PMHKNGSFMGNF
                Brassica napus SEQ ID NO:20 (30) PF  V  L*KTHQPRA  SWG  KKSGTMLNG  VI Dunaliella salina SEQ ID NO:26    (61) STR  QTT  CS---
               Oryza sativa SEQ ID NO:24    (56) VV  ---------
                 Amaranthus SEQ IDNO:25     (58) IVP  QAS  A---
     Chlamydamonas reinhardtii SEQ ID NO:23 (56) RA  V  R-------
                  Calystegia SEQ ID NO:22   (60) SP     R-------
                 Glycine max SEQ ID NO:21   (59) NVG  GNSG  FKVS
                Brassica napus SEQ ID NO:20 (60) RP     TAS  S---
```

CHLOROPLAST TRANSIT PEPTIDES

CROSS-REFERENCE TO RELATED APPLICATIONS

This application claims priority from, and the benefit of, U.S. Provisional Application, 62/207,685, filed on Aug. 20, 2015. The entire contents of which are hereby incorporated by reference.

STATEMENT ACCORDING TO 37 C.F.R. § 1.821(C) OR (E)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

FIELD OF THE DISCLOSURE

This disclosure relates to compositions and methods for genetically encoding and expressing polypeptides that are targeted to chloroplasts of higher plants. In certain embodiments, the disclosure relates to amino acid sequences that target chimeric polypeptides to chloroplasts, and/or nucleic acid molecules encoding the same. In certain embodiments, the disclosure relates to chimeric polypeptides comprising an amino acid sequence that control the transit of the chimeric polypeptides to chloroplasts, and/or nucleic acid molecules encoding the same.

BACKGROUND

Plant cells contain distinct subcellular organelles, referred to generally as "plastids," that are delimited by characteristic membrane systems and perform specialized functions within the cell. Particular plastids are responsible for photosynthesis, as well as the synthesis and storage of certain chemical compounds. All plastids are derived from proplastids that are present in the meristematic regions of the plant. Proplastids may develop into, for example: chloroplasts, etioplasts, chromoplasts, gerontoplasts, leucoplasts, amyloplasts, elaioplasts, and proteinoplasts. Plastids exist in a semi-autonomous fashion within the cell, containing their own genetic system and protein synthesis machinery, but relying upon a close cooperation with the nucleo-cytoplasmic system in their development and biosynthetic activities.

In photosynthetic leaf cells of higher plants the most conspicuous plastids are the chloroplasts. The most essential function of chloroplasts is the performance of the light-driven reactions of photosynthesis. But, chloroplasts also carry out many other biosynthetic processes of importance to the plant cell. For example, all of the cell's fatty acids are made by enzymes located in the chloroplast stroma, using the ATP, NAOPH, and carbohydrates readily available there. Moreover, the reducing power of light-activated electrons drives the reduction of nitrite ($NO_2^-$) to ammonia ($NH_3$) in the chloroplast; this ammonia provides the plant with nitrogen required for the synthesis of amino acids and nucleotides.

The chloroplast also takes part in processes of particular importance in the agrochemical industry. For example, it is known that many herbicides act by blocking functions which are performed within the chloroplast. Recent studies have identified the specific target of several herbicides. For instance, triazine-derived herbicides inhibit photosynthesis by displacing a plastoquinone molecule from its binding site in the 32 kD polypeptide of the photosystem II. This 32 kD polypeptide is encoded in the chloroplast genome and synthesized by the organelle machinery. Mutant plants have been obtained which are resistant to triazine herbicides. These plants contain a mutant 32 kD polypeptide from which the plastoquinone can no longer be displaced by triazine herbicides. Sulfonylureas inhibit acetolactate synthase in the chloroplast. Acetolactate synthase is involved in isoleucine and valine synthesis. Glyphosate inhibits the function of 5-enol pyruvyl-3-phosphoshikimate synthase (EPSPS), which is an enzyme involved in the synthesis of aromatic amino acids. All these enzymes are encoded by the nuclear genome, but they are translocated into the chloroplast where the actual amino acid synthesis takes place.

Most chloroplast proteins are encoded in the nucleus of the plant cell, synthesized as larger precursor proteins in the cytosol, and post-translationally imported into the chloroplast. Import across the outer and inner envelope membranes into the stroma is the major means for entry of proteins destined for the stroma, the thylakoid membrane, and the thylakoid lumen. Localization of imported precursor proteins to the thylakoid membrane and thylakoid lumen is accomplished by four distinct mechanisms, including two that are homologous to bacterial protein transport systems. Thus, mechanisms for protein localization in the chloroplast are in part derived from the prokaryotic endosymbiont. Cline and Henry (1996), *Annu. Rev. Cell. Dev. Biol.* 12:1-26.

Precursor proteins destined for chloroplastic expression contain N-terminal extensions known as chloroplast transit peptides (CTPs). The transit peptide is instrumental for specific recognition of the chloroplast surface and in mediating the post-translational translocation of pre-proteins across the chloroplastic envelope and thence to the various sub-compartments within the chloroplast (e.g., stroma, thylakoid, and thylakoid membrane). These N-terminal transit peptide sequences contain all the information necessary for the import of the chloroplast protein into plastids; the transit peptide sequences are necessary and sufficient for plastid import.

Plant genes reported to have naturally-encoded transit peptide sequences at their N-terminus include the chloroplast small subunit of ribulose-1,5-bisphosphate carboxylase (RuBisCo) (de Castro Silva-Filho et al. (1996), *Plant Mol. Biol.* 30:769-80; Schnell et al. (1991), *J. Biol. Chem.* 266:3335-42); EPSPS (see, e.g., Archer et al. (1990), *J. Bioenerg. and Biomemb.* 22:789-810 and U.S. Pat. Nos. 6,867,293, 7,045,684, and Re. 36,449); tryptophan synthase (Zhao et al. (1995), *J. Biol. Chem.* 270:6081-7); plastocyanin (Lawrence et al. (1997), *J. Biol. Chem.* 272:20357-63); chorismate synthase (Schmidt et al. (1993), *J. Biol. Chem.* 268:27447-57); the light harvesting chlorophyll a/b binding protein (LHBP) (Lamppa et al. (1988), *J. Biol. Chem.* 263:14996-14999); and chloroplast protein of *Arabidopsis thaliana* (Lee et al. (2008), *Plant Cell* 20:1603-22). United States Patent Publication No. US 2010/0071090 provides certain chloroplast targeting peptides from *Chlamydomonas* sp.

However, the structural requirements for the information encoded by chloroplast targeting peptides remains elusive, due to their high level of sequence diversity and lack of common or consensus sequence motifs, though it is possible that there are distinct subgroups of chloroplast targeting peptides with independent structural motifs. Lee et al. (2008), supra. Further, not all of these sequences have been useful in the heterologous expression of chloroplast-targeted proteins in higher plants.

BRIEF SUMMARY OF THE DISCLOSURE

Described herein are compositions and methods for chloroplast targeting of polypeptides in a plant. In some embodiments, compositions comprise a nucleic acid molecule comprising at least one nucleotide sequence encoding a chloroplast transit peptide (e.g., a TraP10, TraP11, TraP17, TraP18, TraP19, TraP26, TraP27, or TraP28 peptide) operably linked to a nucleotide sequence of interest. In particular embodiments, such nucleic acid molecules may be useful for expression and targeting of a polypeptide encoded by the nucleotide sequence of interest in a monocot or dicot plant. Further described are vectors comprising a nucleic acid molecule comprising at least one nucleotide sequence encoding a TraP10, TraP11, TraP17, TraP18, TraP19, TraP26, TraP27, or TraP28 chloroplast transit peptide operably linked to a nucleotide sequence of interest.

In some embodiments, a nucleotide sequence encoding a TraP10, TraP11, TraP17, TraP18, TraP19, TraP26, TraP27, or TraP28 chloroplast transit peptide may be a prokaryotic nucleotide sequence, or a functional variant thereof. In some embodiments, a nucleotide sequence encoding a TraP10, TraP11, TraP17, TraP18, TraP19, TraP26, TraP27, or TraP28 chloroplast transit peptide may be a nucleotide sequence isolated from a lower photosynthetic eukaryote (for example, a sequence isolated from a Chlorophyte, such as *Chlamydomonas* and *Dunaliella*), or a functional variant thereof. In some embodiments, a nucleotide sequence encoding a TraP10, TraP11, TraP17, TraP18, TraP19, TraP26, TraP27, or TraP28 chloroplast transit peptide may be a nucleotide sequence isolated from a higher photosynthetic eukaryote (for example, a sequence isolated from a dicot plant, such as *Brassica napus, Amaranthus, Calystegia*, and *Glycine max*, or a monocot plant, such as *Oryza sativa*), or a functional variant thereof. In specific embodiments, a nucleotide sequence encoding a TraP10, TraP11, TraP17, TraP18, TraP19, TraP26, TraP27, or TraP28 chloroplast transit peptide may be a nucleotide sequence isolated from *Brassica napus, Glycine max, Oryza sativa, Amaranthus, Calystegia*, and *Dunaliella salina* and *Chlamydamonas reinhardtii*. In further embodiments, a nucleotide sequence encoding a TraP10, TraP11, TraP17, TraP18, TraP19, TraP26, TraP27, or TraP28 chloroplast transit peptide may be a chimeric nucleotide sequence comprising a partial prokaryotic TraP10, TraP11, TraP17, TraP18, TraP19, TraP26, TraP27, or TraP28 chloroplast transit peptide nucleotide sequence, or a functional variant thereof. In still further embodiments, a nucleotide sequence encoding a TraP10, TraP11, TraP17, TraP18, TraP19, TraP26, TraP27, or TraP28 chloroplast transit peptide may be a chimeric nucleotide sequence comprising more than one eukaryotic chloroplast transit peptide nucleotide sequences, such as more than one (e.g., two) chloroplast transit peptide nucleotide sequences from different plant species, or functional variants thereof. In still further embodiments, a nucleotide sequence encoding a TraP10, TraP11, TraP17, TraP18, TraP19, TraP26, TraP27, or TraP28 chloroplast transit peptide may be a synthetic nucleotide sequence, which may be designed at least in part by reference to a prokaryotic TraP10, TraP11, TraP17, TraP18, TraP19, TraP26, TraP27, or TraP28 chloroplast transit peptide nucleotide sequence. In still further embodiments, a nucleotide sequence encoding a TraP10, TraP11, TraP17, TraP18, TraP19, TraP26, TraP27, or TraP28 chloroplast transit peptide may be a synthetic nucleotide sequence, which may be designed at least in part by reference to a eukaryotic TraP10, TraP11, TraP17, TraP18, TraP19, TraP26, TraP27, or TraP28 chloroplast transit peptide nucleotide sequence. In still further embodiments, a nucleotide sequence encoding a TraP10, TraP11, TraP17, TraP18, TraP19, TraP26, TraP27, or TraP28 chloroplast transit peptide may be a synthetic nucleotide sequence, which may be designed at least in part by reference to a eukaryotic chloroplast transit peptide nucleotide sequence from an EPSPS gene sequence or any other gene sequence containing a chloroplast transit peptide.

In some embodiments, compositions comprise a nucleic acid molecule comprising at least one means for targeting a polypeptide to a chloroplast operably linked to a nucleotide sequence of interest. In particular embodiments, such nucleic acid molecules may be useful for expression and targeting of a polypeptide encoded by the nucleotide sequence of interest in a monocot or dicot plant. Further described are vectors comprising a nucleic acid molecule comprising at least one means for targeting a polypeptide to a chloroplast operably linked to a nucleotide sequence of interest. Other embodiments describe a means for targeting a polypeptide to a chloroplast via a TraP10, TraP11, TraP17, TraP18, TraP19, TraP26, TraP27, or TraP28 nucleotide sequence and functional equivalents thereof.

Also described herein are plants, plant tissues, and plant cells comprising a nucleic acid molecule comprising at least one nucleotide sequence encoding a TraP10, TraP11, TraP17, TraP18, TraP19, TraP26, TraP27, or TraP28 chloroplast transit peptide operably linked to a nucleotide sequence of interest. In some embodiments, a plant, plant tissue, or plant cell may have such a nucleic acid molecule stably integrated in its genome. In some embodiments, a plant, plant tissue, or plant cell may transiently express such a nucleic acid molecule.

Methods are also described for expressing a nucleotide sequence in chloroplasts of the plant or plant cells. In some embodiments, a nucleic acid molecule comprising at least one nucleotide sequence encoding a TraP10, TraP11, TraP17, TraP18, TraP19, TraP26, TraP27, or TraP28 chloroplast transit peptide operably linked to a nucleotide sequence of interest may be used to transform a plant cell, so that a precursor fusion polypeptide comprising the TraP10, TraP11, TraP17, TraP18, TraP19, TraP26, TraP27, or TraP28 chloroplast transit peptide fused to an expression product of the nucleotide sequence of interest is produced in the cytoplasm of the plant cell, and the fusion polypeptide is then transported in vivo into a chloroplast of the plant cell.

Further described are methods for the production of a transgenic plant comprising a nucleic acid molecule comprising at least one nucleotide sequence encoding a TraP10, TraP11, TraP17, TraP18, TraP19, TraP26, TraP27, or TraP28 chloroplast transit peptide operably linked to a nucleotide sequence of interest. Also described are plant products (e.g., seeds) produced from such transgenic plants.

The foregoing and other features will become more apparent from the following detailed description of several embodiments, which proceeds with reference to the accompanying figures.

BRIEF DESCRIPTION OF THE FIGURES

FIG. 1 provides an mRNA molecule that is representative of particular examples of synthetic CTP-encoding nucleotide sequences (for example, the TraP10, TraP11, TraP17, TraP18, TraP19, TraP26, TraP27, or TraP28 chloroplast transit peptide) operably linked to a nucleotide sequence of interest. In some embodiments, an mRNA molecule (such as the one shown) may be transcribed from a DNA molecule comprising an open reading frame including the synthetic CTP-encoding sequence operably linked to the nucleotide sequence of interest. The nucleotide sequence of interest may be, in some embodiments, a sequence encoding a peptide of interest, for example and without limitation, a marker gene product or peptide to be targeted to a plastid.

FIG. 2 provides an alignment of the predicted chloroplast transit peptides from *Brassica napus, Dunaliella salina, Oryza sativa, Amaranthus, Chlamydamonas reinhardtii, Calystegia* and *Glycine max*. The asterisk indicates where the sequences were split and recombined to form the various chimeric TraP sequences. It should be noted that *Amaranthus* was used in two different chimeric chloroplast transit peptides (TraP18 and TraP19), and was spliced at two different locations within the sequence as shown by the presence of two different asterisks.

SEQUENCE LISTING

Figure 3:
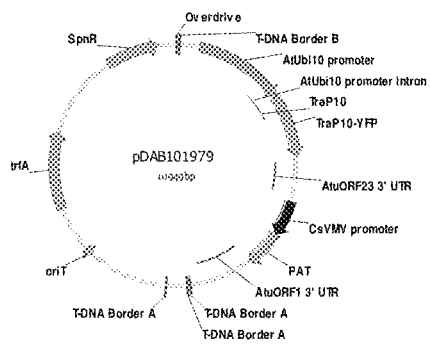
FIG. 3 provides a plasmid map pDAB101979.

The nucleic acid sequences listed in the accompanying Sequence Listing are shown using standard letter abbreviations for nucleotide bases, as defined in 37 C.F.R. § 1.822. Only one strand of each nucleic acid sequence is provided in the accompanying Sequence Listing, but the complementary strand is understood to be included by any reference to the displayed strand. In the accompanying Sequence Listing:

SEQ ID NO:1 shows the amino acid sequence of TraP10.

SEQ ID NO:2 shows the amino acid sequence of TraP11.

SEQ ID NO:3 shows the amino acid sequence of TraP17.

SEQ ID NO:4 shows the amino acid sequence of TraP18.

SEQ ID NO:5 shows the amino acid sequence of TraP19.

SEQ ID NO:6 shows the amino acid sequence of TraP26.

SEQ ID NO:7 shows the amino acid sequence of TraP27.

SEQ ID NO:8 shows the amino acid sequence of TraP28.

SEQ ID NO:9 shows the polynucleotide sequence of TraP10.

SEQ ID NO:10 shows the polynucleotide sequence of TraP11.

SEQ ID NO:11 shows the polynucleotide sequence of TraP17.

SEQ ID NO:12 shows the polynucleotide sequence of TraP18.

SEQ ID NO:13 shows the polynucleotide sequence of TraP19.

SEQ ID NO:14 shows the polynucleotide sequence of TraP26.

SEQ ID NO:15 shows the polynucleotide sequence of TraP27.

SEQ ID NO:16 shows the polynucleotide sequence of TraP28.

DETAILED DESCRIPTION

I. Overview of Several Embodiments

A chloroplast transit peptide (CTP) (or plastid transit peptide) functions co-translationally or post-translationally to direct a polypeptide comprising the CTP to a plastid, for example, a chloroplast. In some embodiments of the invention, either endogenous chloroplast proteins or heterologous proteins may be directed to a chloroplast by expression of such a protein as a larger precursor polypeptide comprising a CTP.

In an exemplary embodiment, a nucleic acid sequence encoding a CTP was isolated from an EPSPS gene sequence obtained from *Brassica napus* (NCBI Database Accession No. P17688), an EPSPS gene sequence obtained from *Glycine max* (NCBI Database Accession No. XP_003517039), an EPSPS gene sequence obtained from *Calystegia* (NCBI Database Accession No. ACB37380), an EPSPS gene sequence obtained from *Chlamydamonas reinhardtii* (NCBI Database Accession No. XP_001702942), an EPSPS gene sequence obtained from *Oryza sativa* (NCBI Database Accession No. AF413082_1), an EPSPS gene sequence obtained from *Amaranthus* (NCBI Database Accession No. ACV53022), and an EPSPS gene sequence obtained from *Dunaliella salina* (NCBI Accession No.: AMBM68632). The CTP was identified and isolated from the full length protein by analyzing the gene sequence with the ChloroP prediction server. Emanuels son et al. (1999), *Protein Science* 8:978-84 (available at cbs.dtu.dk/services/ChloroP). The predicted protein product of the isolated CTP-encoding sequences were used to produce the chimeric CTP-encoding nucleic acid sequences of the subject disclosure, TraP10, TraP11, TraP17, TraP18, TraP19, TraP26, TraP27, or TraP28.

In a further exemplary embodiment, a TraP10 peptide was synthesized independently and fused to a yellow fluorescent protein (YFP) to produce a chimeric TraP10-YFP polypeptide. A nucleic acid molecule encoding the chimeric TraP10-YFP polypeptide was introduced into a binary vector, such that the TraP10-YFP-encoding nucleic acid sequence was operably linked to an AtUbi 10 promoter.

In yet a further exemplary embodiment, a binary vector comprising a TraP10-YFP-encoding nucleic acid sequence operably linked to an AtUbi 10 promoter was transiently transformed into tobacco (*Nicotiana tabacum*) via *Agrobacterium*. Confocal microscopy and Western blot analysis confirmed that TraP10 successfully targeted YFP to tobacco chloroplasts.

In a further exemplary embodiment, a TraP11 peptide was synthesized independently and fused to a yellow fluorescent protein (YFP) to produce a chimeric TraP11-YFP polypeptide. A nucleic acid molecule encoding the chimeric TraP11-YFP polypeptide was introduced into a binary vector, such that the TraP11-YFP-encoding nucleic acid sequence was operably linked to an AtUbi 10 promoter.

In yet a further exemplary embodiment, a binary vector comprising a TraP11-YFP-encoding nucleic acid sequence operably linked to an AtUbi 10 promoter was transiently transformed into tobacco (*Nicotiana tabacum*) via *Agrobacterium*. Confocal microscopy and Western blot analysis confirmed that TraP11 successfully targeted YFP to tobacco chloroplasts.

In a further exemplary embodiment, a TraP17 peptide was synthesized independently and fused to a green fluorescent protein (GFP) to produce a chimeric TraP17-GFP polypeptide. A nucleic acid molecule encoding the chimeric TraP17-GFP polypeptide was introduced into a binary vector, such that the TraP17-GFP-encoding nucleic acid sequence was operably linked to an AtUbi 10 promoter.

In yet a further exemplary embodiment, a binary vector comprising a TraP17-GFP-encoding nucleic acid sequence operably linked to an AtUbi 10 promoter was transiently transformed into maize (*Zea mays*) via *Agrobacterium*. Confocal microscopy and Western blot analysis confirmed that TraP17 successfully targeted GFP to maize chloroplasts.

In a further exemplary embodiment, a TraP18 peptide was synthesized independently and fused to a green fluorescent protein (GFP) to produce a chimeric TraP18-GFP polypeptide. A nucleic acid molecule encoding the chimeric TraP18-GFP polypeptide was introduced into a binary vector, such that the TraP18-GFP-encoding nucleic acid sequence was operably linked to an AtUbi 10 promoter.

In yet a further exemplary embodiment, a binary vector comprising a TraP18-GFP-encoding nucleic acid sequence operably linked to an AtUbi 10 promoter was transiently transformed into maize (*Zea mays*) and tobacco (*Nicotiana tabacum*) via *Agrobacterium*. Confocal microscopy and Western blot analysis confirmed that TraP18 successfully targeted GFP to maize and tobacco chloroplasts.

In a further exemplary embodiment, a TraP19 peptide was synthesized independently and fused to a green fluorescent protein (GFP) to produce a chimeric TraP19-GFP polypeptide. A nucleic acid molecule encoding the chimeric TraP19-GFP polypeptide was introduced into a binary vector, such that the TraP19-GFP-encoding nucleic acid sequence was operably linked to an AtUbi 10 promoter.

In yet a further exemplary embodiment, a binary vector comprising a TraP19-GFP-encoding nucleic acid sequence operably linked to an AtUbi 10 promoter was transiently transformed into maize (*Zea mays*) and tobacco (*Nicotiana tabacum*) via *Agrobacterium*. Confocal microscopy and Western blot analysis confirmed that TraP19 successfully targeted GFP to maize and tobacco chloroplasts.

In a further exemplary embodiment, a TraP26 peptide was synthesized independently and fused to a green fluorescent protein (GFP) to produce a chimeric TraP26-GFP polypeptide. A nucleic acid molecule encoding the chimeric TraP26-GFP polypeptide was introduced into a binary vector, such that the TraP26-GFP-encoding nucleic acid sequence was operably linked to an AtUbi 10 promoter.

In yet a further exemplary embodiment, a binary vector comprising a TraP26-GFP-encoding nucleic acid sequence operably linked to an AtUbi 10 promoter was transiently transformed into tobacco (*Nicotiana tabacum*) via *Agrobacterium*. Confocal microscopy and Western blot analysis confirmed that TraP26 successfully targeted GFP to tobacco chloroplasts.

In a further exemplary embodiment, a TraP27 peptide was synthesized independently and fused to a yellow fluorescent protein (GFP) to produce a chimeric TraP27-GFP polypeptide. A nucleic acid molecule encoding the chimeric TraP27-GFP polypeptide was introduced into a binary vector, such that the TraP27-GFP-encoding nucleic acid sequence was operably linked to an AtUbi 10 promoter.

In yet a further exemplary embodiment, a binary vector comprising a TraP27-GFP-encoding nucleic acid sequence operably linked to an AtUbi 10 promoter was transiently transformed into tobacco (*Nicotiana tabacum*) via *Agrobacterium*. Confocal microscopy and Western blot analysis confirmed that TraP27 successfully targeted GFP to tobacco chloroplasts.

In a further exemplary embodiment, a TraP28 peptide was synthesized independently and fused to a yellow fluorescent protein (GFP) to produce a chimeric TraP28-GFP polypeptide. A nucleic acid molecule encoding the chimeric TraP28-GFP polypeptide was introduced into a binary vector, such that the TraP28-GFP-encoding nucleic acid sequence was operably linked to an AtUbi 10 promoter.

In yet a further exemplary embodiment, a binary vector comprising a TraP28-GFP-encoding nucleic acid sequence operably linked to an AtUbi 10 promoter was transiently transformed into tobacco (*Nicotiana tabacum*) via *Agrobacterium*. Confocal microscopy and Western blot analysis confirmed that TraP28 successfully targeted GFP to tobacco chloroplasts.

In a further exemplary embodiment, nucleic acid sequences, each encoding a synthetic TraP peptide of the invention, were synthesized independently and operably linked to a nucleic acid sequence encoding an agronomically important gene sequence. The TraP sequences can be fused to herbicide tolerant traits (e.g. dgt-28, dgt-14, dgt-32 and dgt-33) to produce synthetic nucleic acid molecules, each encoding a chimeric TraP10:DGT-28, TraP11:DGT-28, TraP17:DGT-28, TraP18:DGT-28, TraP19:DGT-28, TraP26:DGT-28, TraP27:DGT-28 or TraP28:DGT-28 fusion polypeptide. Such nucleic acid molecules, each encoding a chimeric TraP10:DGT-28, TraP11:DGT-28, TraP17:DGT-28, TraP18:DGT-28, TraP19:DGT-28, TraP26:DGT-28, TraP27:DGT-28 or TraP28:DGT-28 polypeptide, can be each introduced into a binary vector, such that each TraP10:DGT-28, TraP11:DGT-28, TraP17:DGT-28, TraP18:DGT-28, TraP19:DGT-28, TraP26:DGT-28, TraP27:DGT-28 or TraP28:DGT-28-encoding nucleic acid sequence was operably linked to a promoter and other gene regulatory elements. The binary containing the TraP10:DGT-28, TraP11:DGT-28, TraP17:DGT-28, TraP18:DGT-28, TraP19:DGT-28, TraP26:DGT-28, TraP27:DGT-28 or TraP28:DGT-28-encoding nucleic acid sequence was used to transform various plant species. The transgenic plants can be assayed for glyphosate tolerance as a result of the expression and translocation of the DGT-28 enzymes to the chloroplast.

In view of the aforementioned detailed working examples, TraP10, TraP11, TraP17, TraP18, TraP19, TraP26, TraP27, or TraP28 sequences of the invention may be used to direct any polypeptide to a plastid in a broad range of plant species. For example, by methods made available to those of skill in the art by the present disclosure, a chimeric polypeptide comprising a TraP10, TraP11, TraP17, TraP18, TraP19, TraP26, TraP27, or TraP28 peptide sequence fused to the N-terminus of any second peptide sequence may be introduced into a host cell for plastid targeting of the second peptide sequence. Thus, in particular embodiments, a TraP10, TraP11, TraP17, TraP18, TraP19, TraP26, TraP27, or TraP28 peptide may provide increased efficiency of import and processing of a peptide for which plastid expression is desired.

II. Abbreviations

CTP chloroplast transit peptide
EPSPS 3-enolpyruvylshikimate-5-phosphate synthase
YFP yellow fluorescent protein
$T_i$ tumor-inducing (plasmids derived from *A. tumefaciens*)
T-DNA transfer DNA III. Terms In order to facilitate review of the various embodiments of the disclosure, the following explanations of specific terms are provided:

Chloroplast transit peptide: As used herein, the term "chloroplast transit peptide" (CTP) (or "plastid transit peptide") may refer to an amino acid sequence that, when present at the N-terminus of a polypeptide, directs the import of the polypeptide into a plastid of a plant cell, e.g., a chloroplast. A CTP is generally necessary and sufficient to direct the import of a protein into a plastid (e.g., a primary, secondary, or tertiary plastid, such as a chloroplast) of a host cell. A putative chloroplast transit peptide may be identified by one of several available algorithms (e.g., PSORT, and ChloroP (available at www.cbs.dtu.dk/services/ChloroP)). ChloroP may provide particularly good prediction of chloroplast transit peptides. Emanuelsson et al. (1999), *Protein Science* 8:978-84. However, prediction of functional chloroplast transit peptides is not achieved at 100% efficiency by any existing algorithm. Therefore, it is important to verify that an identified putative chloroplast transit peptide does indeed function as intended in, e.g., an in vitro, or in vivo methodology.

Chloroplast transit peptides may be located at the N-terminus of a polypeptide that is imported into a plastid, and in some examples may be located at the C-terminus of a polypeptide. The transit peptide may facilitate co- or post-translational transport of a polypeptide comprising the CTP into the plastid. Chloroplast transit peptides typically comprise between about 40 and about 100 amino acids, and such CTPs have been observed to contain certain common characteristics, for example, CTPs contain very few, if any, negatively charged amino acids (such as aspartic acid, glutamic acid, asparagines, or glutamine); the N-terminal regions of CTPs lack charged amino acids, glycine, and proline; the central region of a CTP also is likely to contain a very high proportion of basic or hydroxylated amino acids (such as serine and threonine); and the C-terminal region of a CTP is likely to be rich in arginine, and have the ability to comprise an amphipathic beta-sheet structure. Plastid proteases may cleave the CTP from the remainder of a polypeptide comprising the CTP after importation of the polypeptide into the plastid.

Contact: As used herein, the term "contact with" or "uptake by" a cell, tissue, or organism (e.g., a plant cell; plant tissue; and plant), with regard to a nucleic acid molecule, includes internalization of the nucleic acid molecule into the organism, for example and without limitation: contacting the organism with a composition comprising the nucleic acid molecule; and soaking of organisms with a solution comprising the nucleic acid molecule.

Endogenous: As used herein, the term "endogenous" refers to substances (e.g., nucleic acid molecules and polypeptides) that originate from within a particular organism, tissue, or cell. For example, an "endogenous" polypeptide expressed in a plant cell may refer to a polypeptide that is normally expressed in cells of the same type from non-genetically engineered plants of the same species.

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Genetic material: As used herein, the term "genetic material" includes all genes, and nucleic acid molecules, such as DNA and RNA.

Heterologous: As used herein, the term "heterologous" refers to substances (e.g., nucleic acid molecules and polypeptides) that do not originate from within a particular organism, tissue, or cell. For example, a "heterologous" polypeptide expressed in a plant cell may refer to a polypeptide that is not normally expressed in cells of the same type from non-genetically engineered plants of the same species (e.g., a polypeptide that is expressed in different cells of the same organism or cells of a different organism).

Isolated: As used herein, the term "isolated" refers to molecules (e.g., nucleic acid molecules and polypeptides) that are substantially separated or purified away from other molecules of the same type (e.g., other nucleic acid molecules and other polypeptides) with which the molecule is normally associated in the cell of the organism in which the molecule naturally occurs. For example, an isolated nucleic acid molecule may be substantially separated or purified away from chromosomal DNA or extrachromosomal DNA in the cell of the organism in which the nucleic acid molecule naturally occurs. Thus, the term includes recombinant nucleic acid molecules and polypeptides that are biochemically purified such that other nucleic acid molecules, polypeptides, and cellular components are removed. The term also includes recombinant nucleic acid molecules, chemically-synthesized nucleic acid molecules, and recombinantly produced polypeptides.

The term "substantially purified," as used herein, refers to a molecule that is separated from other molecules normally associated with it in its native state. A substantially purified molecule may be the predominant species present in a composition. A substantially purified molecule may be, for example, at least 60% free, at least 75% free, or at least 90% free from other molecules besides a solvent present in a natural mixture. The term "substantially purified" does not refer to molecules present in their native state.

Nucleic acid molecule: As used herein, the term "nucleic acid molecule" refers to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. Nucleic acid molecules include dimeric (so-called in tandem) forms, and the transcription products of nucleic acid molecules. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; ESTs; and recombinant nucleotide sequences.

In some embodiments, the invention includes nucleotide sequences that may be isolated, purified, or partially purified, for example, using separation methods such as, e.g., ion-exchange chromatography; by exclusion based on molecular size or by affinity; by fractionation techniques based on solubility in different solvents; or methods of genetic engineering such as amplification, cloning, and subcloning.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981), *Adv. Appl. Math.* 2:482; Needleman and Wunsch (1970), *J. Mol. Biol.* 48:443; Pearson and Lipman (1988), *Proc. Natl. Acad. Sci. U.S.A.* 85:2444; Higgins and Sharp (1988), *Gene* 73:237-44; Higgins and Sharp (1989), *CABIOS* 5:151-3; Corpet et al. (1988), *Nucleic Acids Res.* 16:10881-90; Huang et al. (1992), *Comp. Appl. Biosci.* 8:155-65; Pearson et al. (1994), *Methods Mol. Biol.* 24:307-31; Tatiana et al. (1999), *FEMS Microbiol. Lett.* 174:247-50. A detailed consideration of sequence alignment methods and homology calculations can be found in, e.g., Altschul et al. (1990), *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed set to default parameters. Nucleic acid sequences with even greater similarity to the reference sequences will show increasing percentage identity when assessed by this method.

Specifically hybridizable/Specifically complementary: As used herein, the terms "Specifically hybridizable" and "specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC, 0.1% SDS buffer at 65° C. for 16 hours; wash twice in 2×SSC, 0.1% SDS buffer at room temperature for 15 minutes each; and wash twice in 0.5×SSC, 0.1% SDS buffer at 65° C. for 20 minutes each.

Moderate Stringency condition (detects sequences that share at least 80% sequence identity): Hybridization in 5×-6×SSC, 0.1% SDS buffer at 65-70° C. for 16-20 hours; wash twice in 2×SSC, 0.1% SDS buffer at room temperature for 5-20 minutes each; and wash twice in 1×SSC, 0.1% SDS buffer at 55-70° C. for 30 minutes each.

Non-stringent control condition (sequences that share at least 50% sequence identity will hybridize): Hybridization in 6×SSC, 0.1% SDS buffer at room temperature to 55° C. for 16-20 hours; wash at least twice in 2×-3×SSC, 0.1% SDS buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence of SEQ ID NO:9, SEQ ID NO:10, SEQ ID NO:11, SEQ ID NO:12, SEQ ID NO:13, SEQ ID NO:14, SEQ ID NO:15 and SEQ ID NO:16 are those nucleic acid sequences that hybridize under stringent conditions (e.g., the Moderate Stringency conditions set forth, supra) to the reference nucleic acid sequence of SEQ ID NO:9, SEQ ID NO:10, SEQ ID NO:11, SEQ ID NO:12, SEQ ID NO:13, SEQ ID NO:14, SEQ ID NO:15 and SEQ ID NO:16. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is completely complementary to a reference nucleotide sequence will exhibit a sequence identical to the reverse complement sequence of the reference nucleotide sequence. These terms and descriptions are well defined in the art and are easily understood by those of ordinary skill in the art.

When determining the percentage of sequence identity between amino acid sequences, it is well-known by those of skill in the art that the identity of the amino acid in a given position provided by an alignment may differ without affecting desired properties of the polypeptides comprising the aligned sequences. In these instances, the percent sequence identity may be adjusted to account for similarity between conservatively substituted amino acids. These adjustments are well-known and commonly used by those of skill in the art. See, e.g., Myers and Miller (1988), *Computer Applications in Biosciences* 4:11-7.

Thus, embodiments of the invention include functional variants of exemplary plastid transit peptide amino acid sequences, and nucleic acid sequences encoding the same. A functional variant of an exemplary transit peptide sequence may be, for example, a fragment of an exemplary transit peptide amino acid sequence (such as an N-terminal or C-terminal fragment), or a modified sequence of a full-length exemplary transit peptide amino acid sequence or fragment of an exemplary transit peptide amino acid sequence. An exemplary transit peptide amino acid sequence may be modified in some embodiments by introducing one or more conservative amino acid substitutions. A "conservative" amino acid substitution is one in which the amino acid residue is replaced by an amino acid residue having a similar functional side chain, similar size, and/or similar hydrophobicity. Families of amino acids that may be used to replace another amino acid of the same family in order to introduce a conservative substitution are known in the art. For example, these amino acid families include: Basic amino acids (e.g., lysine, arginine, and histidine); acidic amino acids (e.g., aspartic acid and glutamic acid); uncharged (at physiological pH) polar amino acids (e.g., glycine, asparagines, glutamine, serine, threonine, tyrosine, and cytosine); non-polar amino acids (e.g., alanine, valine, leucine, isoleucine, proline, phenylalanine, methionine, and tryptophan); beta-branched amino acids (e.g., threonine, valine, and isoleucine); and aromatic amino acids (e.g., tyrosine, phenylalanine, tryptophan, and histidine). See, e.g., Sambrook et al. (Eds.), supra; and Innis et al., *PCR Protocols: A Guide to Methods and Applications,* 1990, Academic Press, NY, USA.

Operably linked: A first nucleotide sequence is "operably linked" with a second nucleotide sequence when the first nucleotide sequence is in a functional relationship with the second nucleotide sequence. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions.

Any inducible promoter can be used in some embodiments of the invention. See Ward et al. (1993), *Plant Mol. Biol.* 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991), *Proc. Natl. Acad. Sci. USA* 88:0421).

Exemplary constitutive promoters include, but are not limited to: Promoters from plant viruses, such as the 35S promoter from CaMV; promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similarity to said Xba1/NcoI fragment) (International PCT Publication No. WO 96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986), *Nature* 319:791-3); lipofection (Felgner et al. (1987), *Proc. Natl. Acad. Sci. USA* 84:7413-7); microinjection (Mueller et al. (1978), *Cell* 15:579-85); *Agrobacterium*-mediated transfer (Fraley et al. (1983), *Proc. Natl. Acad. Sci. USA* 80:4803-7); direct DNA uptake; and microprojectile bombardment (Klein et al. (1987), *Nature* 327:70).

Transgene: An exogenous nucleic acid sequence. In some examples, a transgene may be a sequence that encodes a polypeptide comprising at least one TraP10, TraP11, TraP17, TraP18, TraP19, TraP26, TraP27, or TraP28 chloroplast transit peptide. In particular examples, a transgene may encode a polypeptide comprising at least one TraP10, TraP11, TraP17, TraP18, TraP19, TraP26, TraP27, or TraP28 chloroplast transit peptide and at least an additional peptide sequence (e.g., a peptide sequence that confers herbicide-resistance), for which plastid expression is desirable. In these and other examples, a transgene may contain regulatory sequences operably linked to a coding sequence of the transgene (e.g., a promoter). For the purposes of this disclosure, the term "transgenic," when used to refer to an organism (e.g., a plant), refers to an organism that comprises the exogenous nucleic acid sequence. In some examples, the organism comprising the exogenous nucleic acid sequence may be an organism into which the nucleic acid sequence was introduced via molecular transformation techniques. In other examples, the organism comprising the exogenous nucleic acid sequence may be an organism into which the nucleic acid sequence was introduced by, for example, introgression or cross-pollination in a plant.

Transport: As used herein, the terms "transport(s)," "target(s)," and "transfer(s)" refers to the property of certain amino acid sequences of the invention that facilitates the movement of a polypeptide comprising the amino acid sequence from the nucleus of a host cell into a plastid of the host cell. In particular embodiments, such an amino acid sequence (i.e., a CTP) may be capable of transporting about 100%, at least about 95%, at least about 90%, at least about 85%, at least about 80%, at least about 70%, at least about 60%, and/or at least about 50% of a polypeptide comprising the amino acid sequence into plastids of a host cell.

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a TraP10, TraP11, TraP17, TraP18, TraP19, TraP26, TraP27, or TraP28-Encoding Sequence In some embodiments, this disclosure provides a nucleic acid molecule comprising at least one nucleotide sequence encoding a TraP10 chloroplast transit peptide operably linked to a nucleotide sequence of interest. In other embodiments, this disclosure provides a nucleic acid molecule comprising at least one nucleotide sequence encoding a TraP11 chloroplast transit peptide operably linked to a nucleotide sequence of interest. In other embodiments, this disclosure provides a nucleic acid molecule comprising at least one nucleotide sequence encoding a TraP17 chloroplast transit peptide operably linked to a nucleotide sequence of interest. In other embodiments, this disclosure provides a nucleic acid molecule comprising at least one nucleotide sequence encoding a TraP18 chloroplast transit peptide operably linked to a nucleotide sequence of interest. In other embodiments, this disclosure provides a nucleic acid molecule comprising at least one nucleotide sequence encoding a TraP19 chloroplast transit peptide operably linked to a nucleotide sequence of interest. In other embodiments, this disclosure provides a nucleic acid molecule comprising at least one nucleotide sequence encoding a TraP26 chloroplast transit peptide operably linked to a nucleotide sequence of interest. In other embodiments, this disclosure provides a nucleic acid molecule comprising at least one nucleotide sequence encoding a TraP27 chloroplast transit peptide operably linked to a nucleotide sequence of interest. In other embodiments, this disclosure provides a nucleic acid molecule comprising at least one nucleotide sequence encoding a TraP28 chloroplast transit peptide operably linked to a nucleotide sequence of interest.

In particular embodiments, the nucleotide sequence of interest may be a nucleotide sequence that encodes a polypeptide of interest. In particular embodiments, a single nucleic acid molecule is provided that encodes a polypeptide wherein a TraP10 peptide sequence is fused to the N-terminus of a polypeptide of interest. In particular embodiments, a single nucleic acid molecule is provided that encodes a polypeptide wherein a TraP11 peptide sequence is fused to the N-terminus of a polypeptide of interest. In particular embodiments, a single nucleic acid molecule is provided that encodes a polypeptide wherein a TraP17 peptide sequence is fused to the N-terminus of a polypeptide of interest. In particular embodiments, a single nucleic acid molecule is provided that encodes a polypeptide wherein a TraP18 peptide sequence is fused to the N-terminus of a polypeptide of interest. In particular embodiments, a single nucleic acid molecule is provided that encodes a polypeptide wherein a TraP19 peptide sequence is fused to the N-terminus of a polypeptide of interest. In particular embodiments, a single nucleic acid molecule is provided that encodes a polypeptide wherein a TraP26 peptide sequence is fused to the N-terminus of a polypeptide of interest. In particular embodiments, a single nucleic acid molecule is provided that encodes a polypeptide wherein a TraP27 peptide sequence is fused to the N-terminus of a polypeptide of interest. In particular embodiments, a single nucleic acid molecule is provided that encodes a polypeptide wherein a TraP28 peptide sequence is fused to the N-terminus of a polypeptide of interest.

In nucleic acid molecules provided in some embodiments of the invention, the last codon of a nucleotide sequence encoding a TraP10, TraP11, TraP17, TraP18, TraP19, TraP26, TraP27, or TraP28 chloroplast transit peptide and the first codon of a nucleotide sequence of interest may be separated by any number of nucleotide triplets, e.g., without coding for a "STOP" codon. In some examples, a sequence encoding the first amino acids of a mature protein normally associated with a transit peptide in a natural precursor polypeptide may be present between the last codon of a nucleotide sequence encoding a TraP10, TraP11, TraP17, TraP18, TraP19, TraP26, TraP27, or TraP28 chloroplast transit peptide and the first codon of a nucleotide sequence of interest. A sequence separating a nucleotide sequence encoding a TraP10, TraP11, TraP17, TraP18, TraP19, TraP26, TraP27, or TraP28 chloroplast transit peptide and the first codon of a nucleotide sequence of interest may, for example, consist of any sequence, such that the amino acid sequence encoded is not likely to significantly alter the translated of the chimeric polypeptide and its translocation to a plastid. In these and further embodiments, the last codon of a nucleotide sequence encoding a TraP10, TraP11, TraP17, TraP18, TraP19, TraP26, TraP27, or TraP28 chloroplast transit peptide may be fused in phase-register with the first codon of the nucleotide sequence of interest directly contiguous thereto, or separated therefrom by no more than a short peptide sequence, such as that encoded by a synthetic nucleotide linker (e.g., a nucleotide linker that may have been used to achieve the fusion).

In some embodiments, it may be desirable to modify the nucleotides of a nucleotide sequence of interest and/or a TraP10, TraP11, TraP17, TraP18, TraP19, TraP26, TraP27, or TraP28-encoding sequence fused thereto in a single coding sequence, for example, to enhance expression of the coding sequence in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991), *Gene* 105: 61-72. Codons may be substituted to reflect the preferred codon usage of a particular host in a process sometimes referred to as "codon optimization." Optimized coding sequences containing codons preferred by a particular prokaryotic or eukaryotic host may be prepared by, for example, to increase the rate of translation or to produce recombinant RNA transcripts having desirable properties (e.g., a longer half-life, as compared with transcripts produced from a non-optimized sequence).

Some embodiments include TraP10 functional variants. TraP10 functional variants include, for example and without limitation: homologs and orthologs of the TraP10 set forth as SEQ ID NO:1; chloroplast transit peptides that comprise a contiguous amino acid sequence within SEQ ID NO:1; truncated TraP10 peptides; longer chloroplast transit peptides that comprise a contiguous amino acid sequence within SEQ ID NO:1; chloroplast transit peptides comprising a contiguous amino acid sequence within SEQ ID NO:1 that has one or more conservative amino acid substitutions; and chloroplast transit peptides comprising a contiguous amino acid sequence within SEQ ID NO:1 that has one or more non-conservative amino acid substitutions that are demonstrated to direct an operably linked peptide to a plastid in a plastid-containing cell.

Some embodiments include TraP11 functional variants. TraP11 functional variants include, for example and without limitation: homologs and orthologs of the TraP11 set forth as SEQ ID NO:2; chloroplast transit peptides that comprise a contiguous amino acid sequence within SEQ ID NO:2; truncated TraP11 peptides; longer chloroplast transit peptides that comprise a contiguous amino acid sequence within SEQ ID NO:2; chloroplast transit peptides comprising a contiguous amino acid sequence within SEQ ID NO:2 that has one or more conservative amino acid substitutions; and chloroplast transit peptides comprising a contiguous amino acid sequence within SEQ ID NO:2 that has one or more non-conservative amino acid substitutions that are demonstrated to direct an operably linked peptide to a plastid in a plastid-containing cell.

Some embodiments include TraP17 functional variants. TraP17 functional variants include, for example and without limitation: homologs and orthologs of the TraP17 set forth as SEQ ID NO:3; chloroplast transit peptides that comprise a contiguous amino acid sequence within SEQ ID NO:3; truncated TraP17 peptides; longer chloroplast transit peptides that comprise a contiguous amino acid sequence within SEQ ID NO:3; chloroplast transit peptides comprising a contiguous amino acid sequence within SEQ ID NO:3 that has one or more conservative amino acid substitutions; and chloroplast transit peptides comprising a contiguous amino acid sequence within SEQ ID NO:3 that has one or more non-conservative amino acid substitutions that are demonstrated to direct an operably linked peptide to a plastid in a plastid-containing cell.

Some embodiments include TraP18 functional variants. TraP18 functional variants include, for example and without limitation: homologs and orthologs of the TraP18 set forth as SEQ ID NO:4; chloroplast transit peptides that comprise a contiguous amino acid sequence within SEQ ID NO:4; truncated TraP18 peptides; longer chloroplast transit peptides that comprise a contiguous amino acid sequence within SEQ ID NO:4; chloroplast transit peptides comprising a contiguous amino acid sequence within SEQ ID NO:4 that has one or more conservative amino acid substitutions; and chloroplast transit peptides comprising a contiguous amino acid sequence within SEQ ID NO:4 that has one or more non-conservative amino acid substitutions that are demonstrated to direct an operably linked peptide to a plastid in a plastid-containing cell.

Some embodiments include TraP19 functional variants. TraP19 functional variants include, for example and without limitation: homologs and orthologs of the TraP19 set forth as SEQ ID NO:5; chloroplast transit peptides that comprise a contiguous amino acid sequence within SEQ ID NO:5; truncated TraP19 peptides; longer chloroplast transit peptides that comprise a contiguous amino acid sequence within SEQ ID NO:5; chloroplast transit peptides comprising a contiguous amino acid sequence within SEQ ID NO:5 that has one or more conservative amino acid substitutions; and chloroplast transit peptides comprising a contiguous amino acid sequence within SEQ ID NO:5 that has one or more non-conservative amino acid substitutions that are demonstrated to direct an operably linked peptide to a plastid in a plastid-containing cell.

Some embodiments include TraP26 functional variants. TraP26 functional variants include, for example and without limitation: homologs and orthologs of the TraP26 set forth as SEQ ID NO:6; chloroplast transit peptides that comprise a contiguous amino acid sequence within SEQ ID NO:6; truncated TraP26 peptides; longer chloroplast transit peptides that comprise a contiguous amino acid sequence within SEQ ID NO:6; chloroplast transit peptides comprising a contiguous amino acid sequence within SEQ ID NO:6 that has one or more conservative amino acid substitutions; and chloroplast transit peptides comprising a contiguous amino acid sequence within SEQ ID NO:6 that has one or more non-conservative amino acid substitutions that are demonstrated to direct an operably linked peptide to a plastid in a plastid-containing cell.

Some embodiments include TraP27 functional variants. TraP27 functional variants include, for example and without limitation: homologs and orthologs of the TraP27 set forth as SEQ ID NO:7; chloroplast transit peptides that comprise a contiguous amino acid sequence within SEQ ID NO:7; truncated TraP27 peptides; longer chloroplast transit peptides that comprise a contiguous amino acid sequence within SEQ ID NO:7; chloroplast transit peptides comprising a contiguous amino acid sequence within SEQ ID NO:7 that has one or more conservative amino acid substitutions; and chloroplast transit peptides comprising a contiguous amino acid sequence within SEQ ID NO:7 that has one or more non-conservative amino acid substitutions that are demonstrated to direct an operably linked peptide to a plastid in a plastid-containing cell.

Some embodiments include TraP28 functional variants. TraP28 functional variants include, for example and without limitation: homologs and orthologs of the TraP28 set forth as SEQ ID NO:8; chloroplast transit peptides that comprise a contiguous amino acid sequence within SEQ ID NO:8; truncated TraP28 peptides; longer chloroplast transit peptides that comprise a contiguous amino acid sequence within SEQ ID NO:8; chloroplast transit peptides comprising a contiguous amino acid sequence within SEQ ID NO:8 that has one or more conservative amino acid substitutions; and chloroplast transit peptides comprising a contiguous amino acid sequence within SEQ ID NO:8 that has one or more non-conservative amino acid substitutions that are demonstrated to direct an operably linked peptide to a plastid in a plastid-containing cell.

Some embodiments of the invention also include a nucleic acid molecule comprising a nucleotide sequence encoding a TraP10, TraP11, TraP17, TraP18, TraP19, TraP26, TraP27, or TraP28 peptide. Such nucleic acid molecules may be useful, for example, in facilitating manipulation of the TraP10, TraP11, TraP17, TraP18, TraP19, TraP26, TraP27, or TraP28-encoding sequence in molecular biology techniques. For example, in some embodiments, a TraP10, TraP11, TraP17, TraP18, TraP19, TraP26, TraP27, or TraP28-encoding sequence may be introduced into a suitable vector for sub-cloning of the sequence into an expression vector, or a TraP10, TraP11, TraP17, TraP18, TraP19, TraP26, TraP27, or TraP28-encoding sequence may be introduced into a nucleic acid molecule that facilitates the production of a further nucleic acid molecule comprising the TraP10, TraP11, TraP17, TraP18, TraP19, TraP26, TraP27, or TraP28-encoding sequence operably linked to a nucleotide sequence of interest.

In particular examples, a TraP10 peptide is equal or less than 72 amino acids in length. For example, a TraP10 peptide may be 72, 71, 70, 69, 68, 67, 66, 65, 64, 63, 62 or fewer amino acids in length. In certain examples, a TraP10 peptide comprises the amino acid sequence set forth in SEQ ID NO:1, or a functional variant thereof. Thus, a TraP10 peptide may comprise an amino acid sequence comprising SEQ ID NO:1, or a functional variant thereof, wherein the length of the TraP10 peptide or functional variant thereof is equal or less than 72 amino acids in length. In certain examples, a TraP10 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:1.

All of the nucleotide sequences that encode, for example, the TraP10 peptide of SEQ ID NO:1, or functional variants thereof comprising less than the entire sequence of SEQ ID NO:1, will be immediately recognizable by those of skill in the art. The degeneracy of the genetic code provides a finite number of coding sequences for a particular amino acid sequence. The selection of a particular sequence to encode a TraP10 peptide is within the discretion of the practitioner. Different coding sequences may be desirable in different applications. For example, to increase expression of the TraP10 peptide in a particular host, a coding sequence may be selected that reflects the codon usage bias of the host. By way of example, a TraP10 peptide may be encoded by the nucleotide sequence set forth as SEQ ID NO:9.

In particular examples, a TraP11 peptide is equal or less than 68 amino acids in length. For example, a TraP11 peptide may be 68, 67, 66, 65, 64, 63, 62, 61, 60, 59, or fewer amino acids in length. In certain examples, a TraP11 peptide comprises the amino acid sequence set forth in SEQ ID NO:2, or a functional variant thereof. Thus, a TraP11 peptide may comprise an amino acid sequence comprising SEQ ID NO:2, or a functional variant thereof, wherein the length of the TraP11 peptide or functional variant thereof is equal or less than 68 amino acids in length. In certain examples, a TraP11 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:2.

All of the nucleotide sequences that encode, for example, the TraP11 peptide of SEQ ID NO:2, or functional variants thereof comprising less than the entire sequence of SEQ ID NO:2, will be immediately recognizable by those of skill in the art. The degeneracy of the genetic code provides a finite number of coding sequences for a particular amino acid sequence. The selection of a particular sequence to encode a TraP11 peptide is within the discretion of the practitioner. Different coding sequences may be desirable in different applications. For example, to increase expression of the TraP11 peptide in a particular host, a coding sequence may be selected that reflects the codon usage bias of the host. By way of example, a TraP11 peptide may be encoded by the nucleotide sequence set forth as SEQ ID NO:10.

In particular examples, a TraP17 peptide is equal or less than 66 amino acids in length. For example, a TraP17 peptide may be 66, 65, 64, 63, 62, 61, 60, 59, 58 or fewer amino acids in length. In certain examples, a TraP17 peptide comprises the amino acid sequence set forth in SEQ ID NO:3, or a functional variant thereof. Thus, a TraP17 peptide may comprise an amino acid sequence comprising SEQ ID NO:3, or a functional variant thereof, wherein the length of the TraP17 peptide or functional variant thereof is equal or less than 66 amino acids in length. In certain examples, a TraP17 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:3.

All of the nucleotide sequences that encode, for example, the TraP17 peptide of SEQ ID NO:3, or functional variants thereof comprising less than the entire sequence of SEQ ID NO:3, will be immediately recognizable by those of skill in the art. The degeneracy of the genetic code provides a finite number of coding sequences for a particular amino acid sequence. The selection of a particular sequence to encode a TraP17 peptide is within the discretion of the practitioner. Different coding sequences may be desirable in different applications. For example, to increase expression of the TraP17 peptide in a particular host, a coding sequence may be selected that reflects the codon usage bias of the host. By way of example, a TraP17 peptide may be encoded by the nucleotide sequence set forth as SEQ ID NO:11.

In particular examples, a TraP18 peptide is equal or less than 67 amino acids in length. For example, a TraP18 peptide may be 67, 66, 65, 64, 63, 62, 61, 60, 59, or fewer amino acids in length. In certain examples, a TraP18 peptide comprises the amino acid sequence set forth in SEQ ID NO:4, or a functional variant thereof. Thus, a TraP18 peptide may comprise an amino acid sequence comprising SEQ ID NO:4, or a functional variant thereof, wherein the length of the TraP18 peptide or functional variant thereof is equal or less than 67 amino acids in length. In certain examples, a TraP18 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:4.

All of the nucleotide sequences that encode, for example, the TraP18 peptide of SEQ ID NO:4, or functional variants thereof comprising less than the entire sequence of SEQ ID NO:4, will be immediately recognizable by those of skill in the art. The degeneracy of the genetic code provides a finite number of coding sequences for a particular amino acid sequence. The selection of a particular sequence to encode a TraP18 peptide is within the discretion of the practitioner. Different coding sequences may be desirable in different applications. For example, to increase expression of the TraP18 peptide in a particular host, a coding sequence may be selected that reflects the codon usage bias of the host. By way of example, a TraP18 peptide may be encoded by the nucleotide sequence set forth as SEQ ID NO:12.

In particular examples, a TraP19 peptide is equal or less than 67 amino acids in length. For example, a TraP19 peptide may be 67, 66, 65, 64, 63, 62, 61, 60, 59, or fewer amino acids in length. In certain examples, a TraP19 peptide comprises the amino acid sequence set forth in SEQ ID NO:5, or a functional variant thereof. Thus, a TraP19 peptide may comprise an amino acid sequence comprising SEQ ID NO:5, or a functional variant thereof, wherein the length of the TraP19 peptide or functional variant thereof is equal or less than 67 amino acids in length. In certain examples, a TraP19 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:5.

All of the nucleotide sequences that encode, for example, the TraP19 peptide of SEQ ID NO:5, or functional variants thereof comprising less than the entire sequence of SEQ ID NO:5, will be immediately recognizable by those of skill in the art. The degeneracy of the genetic code provides a finite number of coding sequences for a particular amino acid sequence. The selection of a particular sequence to encode a TraP19 peptide is within the discretion of the practitioner. Different coding sequences may be desirable in different applications. For example, to increase expression of the TraP19 peptide in a particular host, a coding sequence may be selected that reflects the codon usage bias of the host. By way of example, a TraP19 peptide may be encoded by the nucleotide sequence set forth as SEQ ID NO:13.

In particular examples, a TraP26 peptide is equal or less than 60 amino acids in length. For example, a TraP26 peptide may be 60, 59, 58, 57, 56, 55, 54, 53, 52, 51, or fewer amino acids in length. In certain examples, a TraP26 peptide comprises the amino acid sequence set forth in SEQ ID NO:6, or a functional variant thereof. Thus, a TraP26 peptide may comprise an amino acid sequence comprising SEQ ID NO:6, or a functional variant thereof, wherein the length of the TraP26 peptide or functional variant thereof is equal or less than 60 amino acids in length. In certain examples, a TraP26 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:6.

All of the nucleotide sequences that encode, for example, the TraP26 peptide of SEQ ID NO:6, or functional variants thereof comprising less than the entire sequence of SEQ ID NO:6, will be immediately recognizable by those of skill in the art. The degeneracy of the genetic code provides a finite number of coding sequences for a particular amino acid sequence. The selection of a particular sequence to encode a TraP26 peptide is within the discretion of the practitioner. Different coding sequences may be desirable in different applications. For example, to increase expression of the TraP26 peptide in a particular host, a coding sequence may be selected that reflects the codon usage bias of the host. By way of example, a TraP26 peptide may be encoded by the nucleotide sequence set forth as SEQ ID NO:14.

In particular examples, a TraP27 peptide is equal or less than 61 amino acids in length. For example, a TraP27 peptide may be 61, 60, 59, 58, 57, 56, 55, 54, or fewer amino acids in length. In certain examples, a TraP27 peptide comprises the amino acid sequence set forth in SEQ ID NO:7, or a functional variant thereof. Thus, a TraP27 peptide may comprise an amino acid sequence comprising SEQ ID NO:7, or a functional variant thereof, wherein the length of the TraP27 peptide or functional variant thereof is equal or less than 61 amino acids in length. In certain examples, a TraP27 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:7.

All of the nucleotide sequences that encode, for example, the TraP27 peptide of SEQ ID NO:7, or functional variants thereof comprising less than the entire sequence of SEQ ID NO:7, will be immediately recognizable by those of skill in the art. The degeneracy of the genetic code provides a finite number of coding sequences for a particular amino acid sequence. The selection of a particular sequence to encode a TraP27 peptide is within the discretion of the practitioner. Different coding sequences may be desirable in different applications. For example, to increase expression of the TraP27 peptide in a particular host, a coding sequence may be selected that reflects the codon usage bias of the host. By way of example, a TraP27 peptide may be encoded by the nucleotide sequence set forth as SEQ ID NO:15.

In particular examples, a TraP28 peptide is equal or less than 60 amino acids in length. For example, a TraP28 peptide may be 60, 59, 58, 57, 56, 55, 54, 53, 52, 51, or fewer amino acids in length. In certain examples, a TraP28 peptide comprises the amino acid sequence set forth in SEQ ID NO:8, or a functional variant thereof. Thus, a TraP28 peptide may comprise an amino acid sequence comprising SEQ ID NO:8, or a functional variant thereof, wherein the length of the TraP28 peptide or functional variant thereof is equal or less than 60 amino acids in length. In certain examples, a TraP28 peptide or functional variant thereof may comprise an amino acid sequence that is, e.g., at least 80%, at least 85%, at least 90%, at least 92%, at least 94%, at least 95%, at least 96%, at least 97%, at least 98%, at least 99%, or 100% identical to SEQ ID NO:8.

All of the nucleotide sequences that encode, for example, the TraP28 peptide of SEQ ID NO:8, or functional variants thereof comprising less than the entire sequence of SEQ ID NO:8, will be immediately recognizable by those of skill in the art. The degeneracy of the genetic code provides a finite number of coding sequences for a particular amino acid sequence. The selection of a particular sequence to encode a TraP28 peptide is within the discretion of the practitioner. Different coding sequences may be desirable in different applications. For example, to increase expression of the TraP28 peptide in a particular host, a coding sequence may be selected that reflects the codon usage bias of the host. By way of example, a TraP28 peptide may be encoded by the nucleotide sequence set forth as SEQ ID NO:16.

Any polypeptide may be targeted to a plastid of a plastid-containing cell by incorporation of a TraP10, TraP11, TraP17, TraP18, TraP19, TraP26, TraP27, or TraP28 peptide sequence. For example, a polypeptide may be linked to a TraP10, TraP11, TraP17, TraP18, TraP19, TraP26, TraP27, or TraP28 peptide sequence in some embodiments, so as to direct the polypeptide to a plastid in a cell wherein the linked polypeptide—TraP10, TraP11, TraP17, TraP18, TraP19, TraP26, TraP27, or TraP28 molecule is expressed. In particular embodiments, a polypeptide targeted to a plastid by incorporation of a TraP10, TraP11, TraP17, TraP18, TraP19, TraP26, TraP27, or TraP28 sequence may be, for example, a polypeptide that is normally expressed in a plastid of a cell wherein the polypeptide is natively expressed. For example and without limitation, a polypeptide targeted to a plastid by incorporation of a TraP10, TraP11, TraP17, TraP18, TraP19, TraP26, TraP27, or TraP28 sequence may be a polypeptide involved in herbicide resistance, virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. A polypeptide targeted to a plastid by incorporation of a TraP10, TraP11, TraP17, TraP18, TraP19, TraP26, TraP27, or TraP28 sequence may alternatively be, for example and without limitation, a polypeptide involved in plant vigor or yield (including polypeptides involved in tolerance for extreme temperatures, soil conditions, light levels, water levels, nitrogen levels, and chemical environment), or a polypeptide that may be used as a marker to identify a plant comprising a trait of interest (e.g., a selectable marker gene product, a polypeptide involved in seed color, etc.).

Non-limiting examples of polypeptides involved in herbicide resistance that may be linked to a TraP10, TraP11, TraP17, TraP18, TraP19, TraP26, TraP27, or TraP28 peptide sequence in some embodiments of the invention include: acetolactase synthase (ALS), mutated ALS, and precursors of ALS (see, e.g., U.S. Pat. No. 5,013,659); EPSPS (see, e.g., U.S. Pat. Nos. 4,971,908 and 6,225,114), such as in some embodiments a DGT-28 or a class IV EPSPS, or in other embodiments a CP4 EPSPS or a class III EPSPS; enzymes that modify a physiological process that occurs in a plastid, including photosynthesis, and synthesis of fatty acids, amino acids, oils, arotenoids, terpenoids, starch, etc. Other non-limiting examples of polypeptides that may be linked to a TraP10, TraP11, TraP17, TraP18, TraP19, TraP26, TraP27, or TraP28 peptide in particular embodiments include: zeaxanthin epoxidase, choline monooxygenase, ferrochelatase, omega-3 fatty acid desaturase, glutamine synthetase, starch modifying enzymes, polypeptides involved in synthesis of essential amino acids, provitamin A, hormones, Bt toxin proteins, etc. Nucleotide sequences encoding the aforementioned peptides are available in the art, and such nucleotide sequences may be operably linked to a nucleotide sequence encoding a TraP10, TraP11, TraP17, TraP18, TraP19, TraP26, TraP27, or TraP28 peptide to be expressed into a polypeptide comprising the polypeptide of interest linked to the TraP10, TraP11, TraP17, TraP18, TraP19, TraP26, TraP27, or TraP28 peptide. Furthermore, additional nucleotide sequences encoding any of the aforementioned polypeptides may be identified by those of skill in the art (for example, by cloning of genes with high homology to other genes encoding the particular polypeptide). Once such a nucleotide sequence has been identified, a second nucleotide sequence comprising a TraP10, TraP11, TraP17, TraP18, TraP19, TraP26, TraP27, or TraP28-encoding sequence operably linked to the identified nucleotide sequence, or a sequence encoding an equivalent polypeptide can be designed.

V. Expression of Polypeptides Comprising a TraP10, TraP11, TraP17, TraP18, TraP19, TraP26, TraP27, or TraP28 Chloroplast Transit Peptide In some embodiments, at least one nucleic acid molecule(s) comprising a nucleotide sequence encoding a polypeptide comprising at least one TraP10, TraP11, TraP17, TraP18, TraP19, TraP26, TraP27, or TraP28 chloroplast transit peptide may be introduced into a cell, tissue, or organism for expression of the polypeptide therein. In particular embodiments, a nucleic acid molecule may comprise a nucleotide sequence of interest operably linked to a nucleotide sequence encoding a TraP10, TraP11, TraP17, TraP18, TraP19, TraP26, TraP27, or TraP28 chloroplast transit peptide. For example, a nucleic acid molecule may comprise a coding sequence encoding a polypeptide comprising at least one TraP10, TraP11, TraP17, TraP18, TraP19, TraP26, TraP27, or TraP28 chloroplast transit peptide and at least an additional peptide sequence encoded by a nucleotide sequence of interest. In some embodiments, a nucleic acid molecule of the invention may be introduced into a plastid-containing host cell, tissue, or organism (e.g., a plant cell, plant tissue, and plant), such that a polypeptide may be expressed from the nucleic acid molecule in the plastid-containing host cell, tissue, or organism, wherein the expressed polypeptide comprises at least one TraP10, TraP11, TraP17, TraP18, TraP19, TraP26, TraP27, or TraP28 chloroplast transit peptide and at least an additional peptide sequence encoded by a nucleotide sequence of interest. In certain embodiments, the TraP10, TraP11, TraP17, TraP18, TraP19, TraP26, TraP27, or TraP28 chloroplast transit peptide of such an expressed polypeptide may facilitate targeting of a portion of the polypeptide comprising at least the additional peptide sequence to a plastid of the host cell, tissue, or organism.

In some embodiments, a nucleic acid molecule of the invention may be introduced into a plastid-containing cell by one of any of the methodologies known to those of skill in the art. In particular embodiments, a host cell, tissue, or organism may be contacted with a nucleic acid molecule of the invention in order to introduce the nucleic acid molecule into the cell, tissue, or organism. In particular embodiments, a cell may be transformed with a nucleic acid molecule of the invention such that the nucleic acid molecule is introduced into the cell, and the nucleic acid molecule is stably integrated into the genome of the cell. In some embodiments, a nucleic acid molecule comprising at least one nucleotide sequence encoding a TraP10, TraP11, TraP17, TraP18, TraP19, TraP26, TraP27, or TraP28 chloroplast transit peptide operably linked to a nucleotide sequence of interest may be used for transformation of a cell, for example, a plastid-containing cell (e.g., a plant cell). In order to initiate or enhance expression, a nucleic acid molecule may comprise one or more regulatory sequences, which regulatory sequences may be operably linked to the nucleotide sequence encoding a polypeptide comprising at least one TraP10, TraP11, TraP17, TraP18, TraP19, TraP26, TraP27, or TraP28 chloroplast transit peptide.

A nucleic acid molecule may, for example, be a vector system including, for example, a linear or a closed circular plasmid. In particular embodiments, the vector may be an expression vector. Nucleic acid sequences of the invention may, for example, be inserted into a vector, such that the nucleic acid sequence is operably linked to one or more regulatory sequences. Many vectors are available for this purpose, and selection of the particular vector may depend, for example, on the size of the nucleic acid to be inserted into the vector and the particular host cell to be transformed with the vector. A vector typically contains various components, the identity of which depend on a function of the vector (e.g., amplification of DNA and expression of DNA), and the particular host cell(s) with which the vector is compatible.

Some embodiments may include a plant transformation vector that comprises a nucleotide sequence comprising at least one of the above-described regulatory sequences operatively linked to one or more nucleotide sequence(s) encoding a polypeptide comprising at least one TraP10, TraP11, TraP17, TraP18, TraP19, TraP26, TraP27, or TraP28 chloroplast transit peptide. The one or more nucleotide sequences may be expressed, under the control of the regulatory sequence(s), in a plant cell, tissue, or organism to produce a polypeptide comprising a TraP10, TraP11, TraP17, TraP18, TraP19, TraP26, TraP27, or TraP28 chloroplast transit peptide that targets at least a portion of the polypeptide to a plastid of the plant cell, tissue, or organism.

In some embodiments, a regulatory sequence operably linked to a nucleotide sequence encoding a polypeptide comprising at least one TraP10, TraP11, TraP17, TraP18, TraP19, TraP26, TraP27, or TraP28 chloroplast transit peptide, may be a promoter sequence that functions in a host cell, such as a bacterial cell wherein the nucleic acid molecule is to be amplified, or a plant cell wherein the nucleic acid molecule is to be expressed. Promoters suitable for use in nucleic acid molecules of the invention include those that are inducible, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter).

Additional exemplary promoters include the nopaline synthase (NOS) promoter (Ebert et al. (1987), *Proc. Natl. Acad. Sci. USA* 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987), *Plant Mol. Biol.* 9:315-24); the CaMV 35S promoter (Odell et al. (1985), *Nature* 313: 810-2; the figwort mosaic virus 35S-promoter (Walker et al. (1987), *Proc. Natl. Acad. Sci. USA* 84(19):6624-8); the sucrose synthase promoter (Yang and Russell (1990), *Proc. Natl. Acad. Sci. USA* 87:4144-8); the R gene complex promoter (Chandler et al. (1989), *Plant Cell* 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982), *J. Mol. Appl. Genet.* 1:561-73; Bevan et al. (1983), *Nature* 304:184-7).

In particular embodiments, nucleic acid molecules of the invention may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (see, e.g., U.S. Pat. No. 7,141,424, and International PCT Publication No. WO 99/042587); ovule-specific promoters; (see, e.g., U.S. Patent Application No. 2001/047525 A1); fruit-specific promoters (see, e.g., U.S. Pat. Nos. 4,943,674, and 5,753,475); and seed-specific promoters (see, e.g., U.S. Pat. Nos. 5,420,034, and 5,608,152). In some embodiments, a developmental stage-specific promoter (e.g., a promoter active at a later stage in development) may be used in a composition or method of the invention.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995), *Molecular Biotech.* 3(3):225- 36. Non-limiting examples of 5' UTRs are provided by: GmHsp (U.S. Pat. No. 5,659,122); PhDnaK (U.S. Pat. No. 5,362,865); AtAnt1; TEV (Carrington and Freed (1990), *J. Virol.* 64:1590-7); and AGRtunos (GenBank Accession No. V00087; and Bevan et al. (1983), *Nature* 304:184-7).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983), *Proc. Natl. Acad. Sci. USA* 80:4803-7). An example of the use of different 3' nontranslated regions is provided in Ingelbrecht et al., (1989), *Plant Cell* 1:671-80. Non-limiting examples of polyadenylation signals include one from a *Pisum sativum* RbcS2 gene (Ps.RbcS2-E9; Coruzzi et al. (1984), *EMBO J.* 3:1671-9) and AGRtu.nos (GenBank Accession No. E01312).

A recombinant nucleic acid molecule or vector of the present invention may comprise a selectable marker that confers a selectable phenotype on a transformed cell, such as a plant cell. Selectable markers may also be used to select for plants or plant cells that comprise recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987), *Plant Mol. Biol. Rep.* 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In $18^{th}$ *Stadler Genetics Symposium*, P. Gustafson and R. Appels, eds. (New York: Plenum), pp. 263-82); a β-lactamase gene (Sutcliffe et al. (1978), *Proc. Natl. Acad. Sci. USA* 75:3737-41); a gene which encodes an enzyme for which various chromogenic substrates are known (e.g., PADAC, a chromogenic cephalosporin); a luciferase gene (Ow et al. (1986), *Science* 234:856-9); a xylE gene that encodes a catechol dioxygenase that can convert chromogenic catechols (Zukowski et al. (1983), *Gene* 46(2-3):247-55); an amylase gene (Ikatu et al. (1990), *Bio/Technol.* 8:241-2); a tyrosinase gene which encodes an enzyme capable of oxidizing tyrosine to DOPA and dopaquinone which in turn condenses to melanin (Katz et al. (1983), *J. Gen. Microbiol.* 129:2703-14); and an α-galactosidase.

Suitable methods for transformation of host cells include any method by which DNA can be introduced into a cell, for example and without limitation: by transformation of protoplasts (see, e.g., U.S. Pat. No. 5,508,184); by desiccation/inhibition-mediated DNA uptake (see, e.g., Potrykus et al. (1985), *Mol. Gen. Genet.* 199:183-8); by electroporation (see, e.g., U.S. Pat. No. 5,384,253); by agitation with silicon carbide fibers (see, e.g., U.S. Pat. Nos. 5,302,523 and 5,464,765); by *Agrobacterium*-mediated transformation (see, e.g., U.S. Pat. Nos. 5,563,055, 5,591,616, 5,693,512, 5,824,877, 5,981,840, and 6,384,301); and by acceleration of DNA-coated particles (see, e.g., U.S. Pat. Nos. 5,015,580, 5,550,318, 5,538,880, 6,160,208, 6,399,861, and 6,403,865); etc. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or nucleic acid sequences of the invention in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the vir region, is responsible for T-DNA transfer. The T-DNA region is bordered by terminal repeats. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a TraP10, TraP11, TraP17, TraP18, TraP19, TraP26, TraP27, or TraP28-encoding nucleic acid.

Thus, in some embodiments, a plant transformation vector is derived from a Ti plasmid of *A. tumefaciens* (see, e.g., U.S. Pat. Nos. 4,536,475, 4,693,977, 4,886,937, and 5,501,967; and European Patent EP 0 122 791) or a Ri plasmid of *A. rhizogenes*. Additional plant transformation vectors include, for example and without limitation, those described by Herrera-Estrella et al. (1983), *Nature* 303:209-13; Bevan et al. (1983), *Nature* 304:184-7; Klee et al. (1985), *Bio/Technol.* 3:637-42; and in European Patent EP 0 120 516, and those derived from any of the foregoing. Other bacteria such as *Sinorhizobium*, *Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one TraP10, TraP11, TraP17, TraP18, TraP19, TraP26, TraP27, or TraP28 chloroplast transit peptide) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002), *Plant J.* 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are most likely heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $T_0$ plant, to produce $T_1$ seed. One fourth of the $T_1$ seed produced will be homozygous with respect to the transgene. Germinating $T_1$ seed results in plants that can be tested for heterozygosity, typically using a SNP assay or a PCR-based amplification assay that allows for the distinction between heterozygotes and homozygotes (i.e., a zygosity assay).

In particular embodiments, copies of at least one polypeptide comprising at least one TraP10, TraP11, TraP17, TraP18, TraP19, TraP26, TraP27, or TraP28 chloroplast transit peptide are produced in a plastid-containing cell, into which has been introduced at least one nucleic acid molecule(s) comprising a nucleotide sequence encoding the at least one polypeptide comprising at least one TraP10, TraP11, TraP17, TraP18, TraP19, TraP26, TraP27, or TraP28 chloroplast transit peptide. Each polypeptide comprising at least one TraP10, TraP11, TraP17, TraP18, TraP19, TraP26, TraP27, or TraP28 chloroplast transit peptide may be expressed from multiple nucleic acid sequences introduced in different transformation events, or from a single nucleic acid sequence introduced in a single transformation event. In some embodiments, a plurality of such polypeptides is expressed under the control of a single promoter. In other embodiments, a plurality of such polypeptides is expressed under the control of multiple promoters. Single polypeptides may be expressed that comprise multiple peptide sequences, each of which peptide sequences is to be targeted to a plastid.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence encoding a polypeptide comprising at least one TraP10, TraP11, TraP17, TraP18, TraP19, TraP26, TraP27, or TraP28 chloroplast transit peptide may be introduced into a first plant line that is amenable to transformation, to produce a transgenic plant, which transgenic plant may be crossed with a second plant line to introgress the nucleotide sequence that encodes the polypeptide into the second plant line.

VI. Plant Materials Comprising a TraP10, TraP11, TraP17, TraP18, TraP19, TraP26, TraP27, or TraP28 Chloroplast Transit Peptide-Directed Polypeptide In some embodiments, a plant is provided, wherein the plant comprises a plant cell comprising a nucleotide sequence encoding a polypeptide comprising at least one TraP10, TraP11, TraP17, TraP18, TraP19, TraP26, TraP27, or TraP28 chloroplast transit peptide. In particular embodiments, such a plant may be produced by transformation of a plant tissue or plant cell, and regeneration of a whole plant. In further embodiments, such a plant may be obtained from a commercial source, or through introgression of a nucleic acid comprising a nucleotide sequence encoding a polypeptide comprising at least one TraP10, TraP11, TraP17, TraP18, TraP19, TraP26, TraP27, or TraP28 chloroplast transit peptide into a germplasm. Plant materials comprising a plant cell comprising a nucleotide sequence encoding a polypeptide comprising at least one TraP10, TraP11, TraP17, TraP18, TraP19, TraP26, TraP27, or TraP28 chloroplast transit peptide are also provided. Such a plant material may be obtained from a plant comprising the plant cell. In further embodiments, the plant material is a plant cell that is incapable of regeneration to produce a plant.

A transgenic plant or plant material comprising a nucleotide sequence encoding a polypeptide comprising at least one TraP10, TraP11, TraP17, TraP18, TraP19, TraP26, TraP27, or TraP28 chloroplast transit peptide may in some embodiments exhibit one or more of the following characteristics: expression of the polypeptide in a cell of the plant; expression of a portion of the polypeptide in a plastid of a cell of the plant; import of the polypeptide from the cytosol of a cell of the plant into a plastid of the cell; plastid-specific expression of the polypeptide in a cell of the plant; and/or localization of the polypeptide in a cell of the plant. Such a plant may additionally have one or more desirable traits other than expression of the encoded polypeptide. Such traits may include, for example: resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid molecule of the invention. Accordingly, the plant may be a dicot or monocot. Non-limiting examples of dicotyledonous plants usable in the present methods include *Arabidopsis*, alfalfa, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, *Brassica*, onion, rice, sorghum, wheat, rye, millet, sugarcane, oat, triticale, switchgrass, and turfgrass. Transgenic plants according to the invention may be used or cultivated in any manner.

Some embodiments also provide commodity products containing one or more nucleotide sequences encoding a polypeptide comprising at least one TraP10, TraP11, TraP17, TraP18, TraP19, TraP26, TraP27, or TraP28 chloroplast transit peptide, for example, a commodity product produced from a recombinant plant or seed containing one or more of such nucleotide sequences. Commodity products containing one or more nucleotide sequences encoding a polypeptide comprising at least one TraP10, TraP11, TraP17, TraP18, TraP19, TraP26, TraP27, or TraP28 chloroplast transit peptide include, for example and without limitation: food products, meals, oils, or crushed or whole grains or seeds of a plant comprising one or more nucleotide sequences encoding a polypeptide comprising at least one TraP10, TraP11, TraP17, TraP18, TraP19, TraP26, TraP27, or TraP28 chloroplast transit peptide. The detection of one or more nucleotide sequences encoding a polypeptide comprising at least one TraP10, TraP11, TraP17, TraP18, TraP19, TraP26, TraP27, or TraP28 chloroplast transit peptide in one or more commodity or commodity products is de facto evidence that the commodity or commodity product was at least in part produced from a plant comprising one or more nucleotide sequences encoding a polypeptide comprising at least one TraP10, TraP11, TraP17, TraP18, TraP19, TraP26, TraP27, or TraP28 chloroplast transit peptide. In particular embodiments, a commodity product of the invention comprise a detectable amount of a nucleic acid sequence encoding a polypeptide comprising at least one TraP10, TraP11, TraP17, TraP18, TraP19, TraP26, TraP27, or TraP28 chloroplast transit peptide. In some embodiments, such commodity products may be produced, for example, by obtaining transgenic plants and preparing food or feed from them.

In some embodiments, a transgenic plant or seed comprising a transgene comprising a nucleotide sequence encoding a polypeptide comprising at least one TraP10, TraP11, TraP17, TraP18, TraP19, TraP26, TraP27, or TraP28 chloroplast transit peptide also may comprise at least one other transgenic event in its genome, including without limitation: a transgenic event from which is transcribed an RNAi molecule; a gene encoding an insecticidal protein (e.g., an *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

VII. TraP10, TraP11, TraP17, TraP18, TraP19, TraP26, TraP27, or TraP28-Mediated Localization of Gene Products to Plastids Some embodiments of the present invention provide a method for expression and/or localization of a gene product to a plastid (e.g., a chloroplast). In particular embodiments, the gene product may be a marker gene product, for example, a fluorescent molecule. Expression of the gene product as part of a polypeptide also comprising a TraP10, TraP11, TraP17, TraP18, TraP19, TraP26, TraP27, or TraP28 peptide may provide a system to evaluate the plastid-localizing capabilities of a particular TraP10, TraP11, TraP17, TraP18, TraP19, TraP26, TraP27, or TraP28 peptide sequence. In some embodiments, expression of a marker gene product as part of a TraP10, TraP11, TraP17, TraP18, TraP19, TraP26, TraP27, or TraP28-containing polypeptide is utilized to target expression of the marker gene product to a plastid of a cell wherein the polypeptide is expressed. In certain embodiments, such a marker gene product is localized in plastid(s) of the host cell. For example, the marker gene product may be expressed at higher levels in the plastid(s) than in the cytosol or other organelles of the host cell; the marker gene product may be expressed at much higher levels in the plastid(s); the marker gene product may be expressed essentially only in the plastid(s); or the marker gene product may be expressed entirely in the plastid(s), such that expression in the cytosol or non-plastid organelles cannot be detected.

In some embodiments, a polypeptide comprising a functional TraP10, TraP11, TraP17, TraP18, TraP19, TraP26, TraP27, or TraP28 variant peptide linked to a marker gene product is used to evaluate the characteristics of the functional TraP10, TraP11, TraP17, TraP18, TraP19, TraP26, TraP27, or TraP28 variant peptide. For example, the sequence of a TraP10, TraP11, TraP17, TraP18, TraP19, TraP26, TraP27, or TraP28 peptide may be varied, e.g., by introducing at least one conservative mutation(s) into the TraP10, TraP11, TraP17, TraP18, TraP19, TraP26, TraP27, or TraP28 peptide, and the resulting TraP10, TraP11, TraP17, TraP18, TraP19, TraP26, TraP27, or TraP28 variant peptide may be linked to a marker gene product. After expression in a suitable host cell (for example, a cell wherein one or more regulatory elements in the expression construct are operable), expression of the marker gene product may be determined. By comparing the sub-cellular localization of the marker gene product between the reference TraP peptide-marker construct and the variant TraP peptide-marker construct, it may be determined whether the variant TraP10, TraP11, TraP17, TraP18, TraP19, TraP26, TraP27, or TraP28 peptide provides, for example, greater plastid localization, substantially identical plastid localization, or lesser plastid localization. By identifying TraP10, TraP11, TraP17, TraP18, TraP19, TraP26, TraP27, or TraP28 variants that provide greater plastic localization, the mutations in such TraP10, TraP11, TraP17, TraP18, TraP19, TraP26, TraP27, or TraP28 variants may be incorporated into further TraP10, TraP11, TraP17, TraP18, TraP19, TraP26, TraP27, or TraP28 variants. Performing multiple rounds of this evaluation process, and subsequently incorporating identified favorable mutations in a TraP10, TraP11, TraP17, TraP18, TraP19, TraP26, TraP27, or TraP28 sequence, may yield an iterative process for optimization of a TraP10, TraP11, TraP17, TraP18, TraP19, TraP26, TraP27, or TraP28 sequence. Such optimized TraP10, TraP11, TraP17, TraP18, TraP19, TraP26, TraP27, or TraP28 peptide sequences, and nucleotide sequences encoding the same, are considered part of the present invention, whether or not such optimized TraP10, TraP11, TraP17, TraP18, TraP19, TraP26, TraP27, or TraP28 peptide sequences may be further optimized by additional mutation.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1: Design and Production of Chimeric Chloroplast Transit Peptide (TraP) Sequences Plastids are cytoplasmic organelles found in higher plant species and are present in all plant tissues. Chloroplasts are a specific type of plastid found in green photosynthetic tissues which are responsible for essential physiological functions. For example, one such primary physiological function is the synthesis of aromatic amino acids required by the plant. Nuclear encoded enzymes are required in this biosynthetic pathway and are transported from the cytoplasm to the interior of the chloroplast. These nuclear encoded enzymes usually possess an N-terminal transit peptide that interacts with the chloroplast membrane to facilitate transport of the peptide to the stroma of the chloroplast. Bruce B, (2000) Chloroplast transit peptides: structure, function, and evolution. *Trends Cell Bio.,* 10: 440-447. Upon import, stromal peptidases cleave the transit peptide, leaving the mature functional protein imported within the chloroplast. Richter S, Lamppa G K, (1999) Stromal processing peptidase binds transit peptides and initiates their ATP-dependent turnover in chloroplasts. *Journ. Cell Bio.,* 147: 33-43. The chloroplast transit peptides are variable sequences which are highly divergent in length, composition and organization (Bruce, 2000). The sequence similarities of chloroplast transit peptides diverge significantly amongst homologous proteins from different plant species. The amount of divergence between chloroplast transit peptides is unexpected given that the homologous proteins obtained from different plant species typically share relatively high levels of sequence similarity when comparing the processed mature functional protein.

Novel chimeric chloroplast transit peptide sequences were designed, produced and tested in planta. The novel chimeric chloroplast transit peptides were shown to possess efficacious translocation and processing properties for the import of agronomic important proteins within the chloroplast. Initially, protein sequences from different plant and bacterial species were analyzed via the ChloroP™ computer program to identify putative chloroplast transit peptide sequences (Emanuelsson O, Nielsen H, von Heijne G, (1999) ChloroP, a neural network-based method for predicting chloroplast transit peptides and their cleavage sites. Protein Science, 8: 978-984, available the internet.) After the native chloroplast transit peptides were identified the chloroplast transit peptide sequences were aligned with one another (FIG. 2).

Utilizing the chloroplast transit peptide sequence alignments, novel chimeric chloroplast transit peptides were designed by combining a first half of the chloroplast transit peptide sequence from a first organism with a second half of the chloroplast transit peptide sequence from a second organism in an approximate ratio of 1:1. Exemplary protein sequences of the newly designed chimeric chloroplast transit peptides are TraP10 (SEQ ID NO:1), TraP11 (SEQ ID NO:2), TraP17 (SEQ ID NO:3), TraP18 (SEQ ID NO:4), and TraP19 (SEQ ID NO:5). These novel chimeric chloroplast transit peptide sequences are derived from the EPSPS proteins of *Brassica napus, Glycine max, Oryza sativa, Amaranthus, Calystegia,* and *Dunaliella salina* and *Chlamydamonas reinhardtii*. The TraP10 (SEQ ID NO:1) chimeric chloroplast transit peptide sequence comprises an N-terminus which is derived from *Brassica napus,* and the C-terminus of the chloroplast transit peptide is derived from *Glycine max*. The TraP11 (SEQ ID NO:2) chloroplast transit peptide sequence comprises an N-terminus which is derived from *Glycine max,* and the C-terminus of the chloroplast transit peptide is derived from *Brassica napus*. The TraP17 (SEQ ID NO:3) chloroplast transit peptide sequence comprises an N-terminus which is derived from *Calystegia,* and the C-terminus of the chloroplast transit peptide is derived from *Chlamydamonas reinhardtii*. The TraP18 (SEQ ID NO:4) chloroplast transit peptide sequence comprises an N-terminus which is derived from *Oryza sativa,* and the C-terminus of the chloroplast transit peptide is derived from *Amaranthus*. The TraP19 (SEQ ID NO:5) chloroplast transit peptide sequence comprises an N-terminus which is derived from *Amaranthus,* and the C-terminus of the chloroplast transit peptide is derived from *Dunaliella salina*.

Likewise, multiple protein sequences from different plant species were analyzed via the ChloroP™ (Emanuelsson, 1999) computer program to identify putative chloroplast transit peptide sequences, available on the internet. Utilizing the chloroplast transit peptide sequence alignments, novel synthetic chloroplast transit peptides were designed by randomly selecting amino acids to produce a novel synthetic putative chloroplast transit peptide sequence. Exemplary sequences of the newly designed synthetic chloroplast transit peptides are TraP26 (SEQ ID NO:6), TraP27 (SEQ ID NO:7) and TraP28 (SEQ ID NO:8).

The chimeric chloroplast transit peptides were tested via multiple assays which included a transient in planta expression system and transgenically as stable transformation events that contained a gene regulatory expression element fused to an agronomic important transgene sequence.

Figure 4:
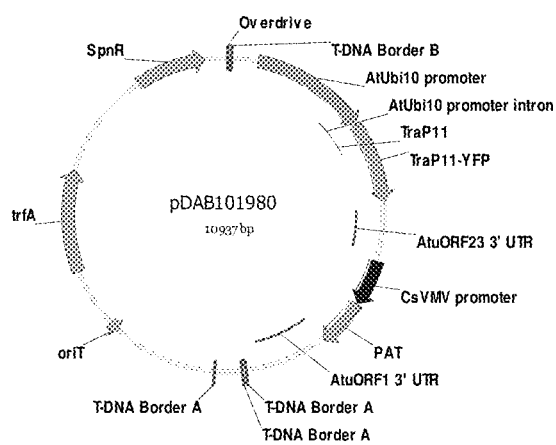
FIG. 4 provides a plasmid map pDAB101980.
Figure 5:
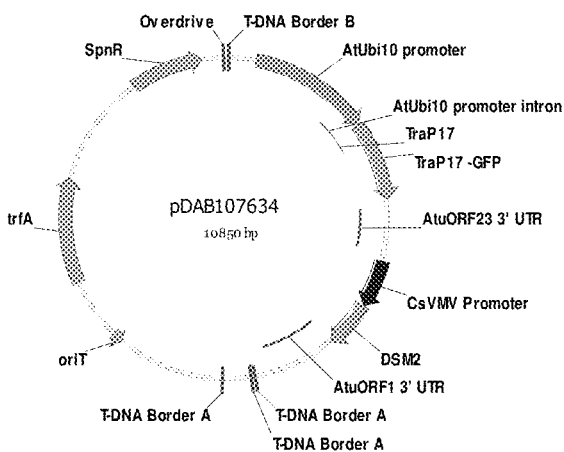
FIG. 5 provides a plasmid map pDAB107634.
Figure 6:
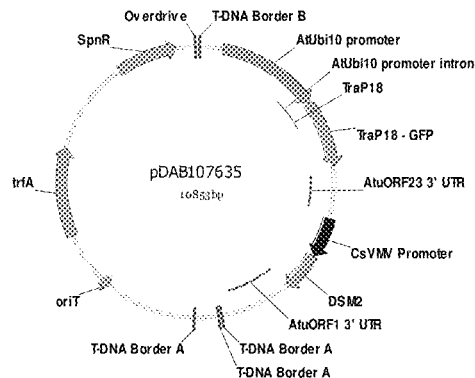
FIG. 6 provides a plasmid map pDAB107635.
Figure 7:
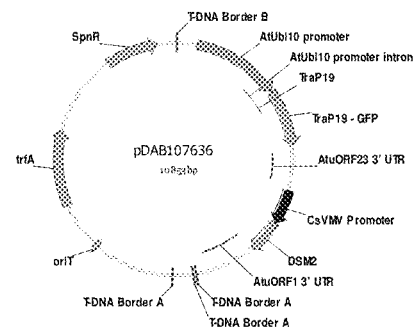
FIG. 7 provides a plasmid map pDAB107636.
Figure 8:
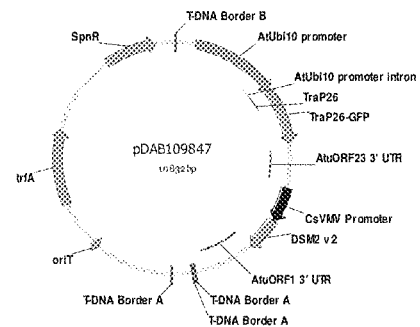
FIG. 8 provides a plasmid map pDAB109847.
Figure 9:
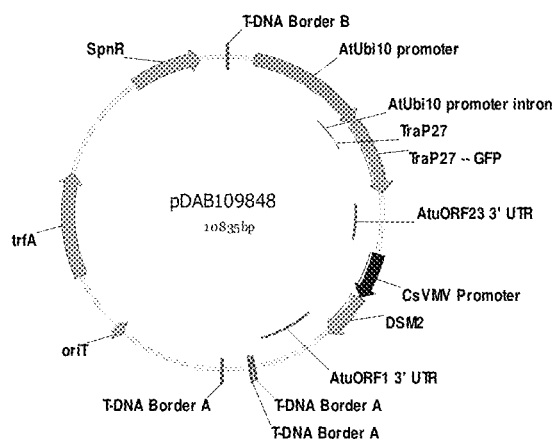
FIG. 9 provides a plasmid map pDAB109848.
Figure 10:
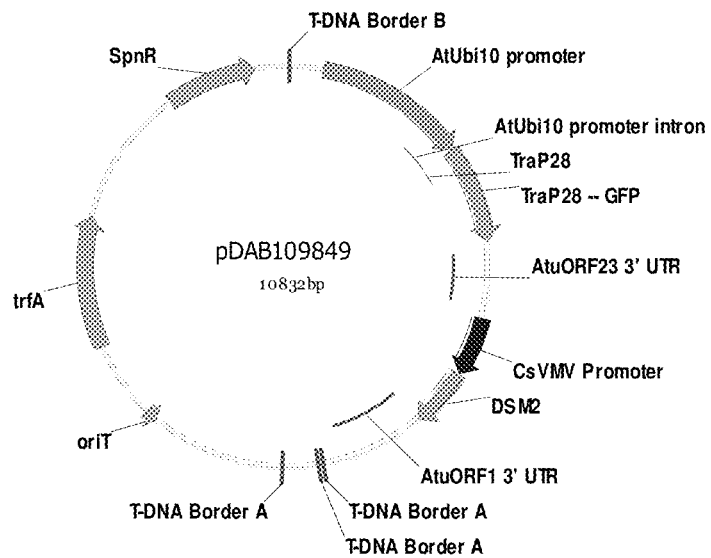
FIG. 10 provides a plasmid map pDAB109849.
Figure 11:
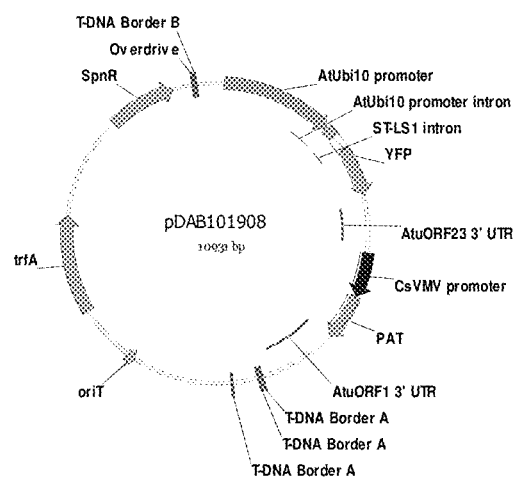
FIG. 11 provides a plasmid map pDAB101908.
Figure 12:
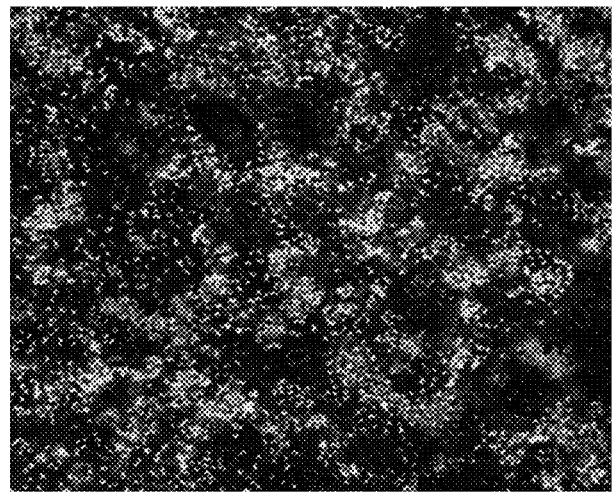
FIG. 12 provides a microscopy image of TraP10-YFP infiltrated into tobacco leaf tissues and translocated into the chloroplasts of the tobacco leaf tissues.
Figure 13:
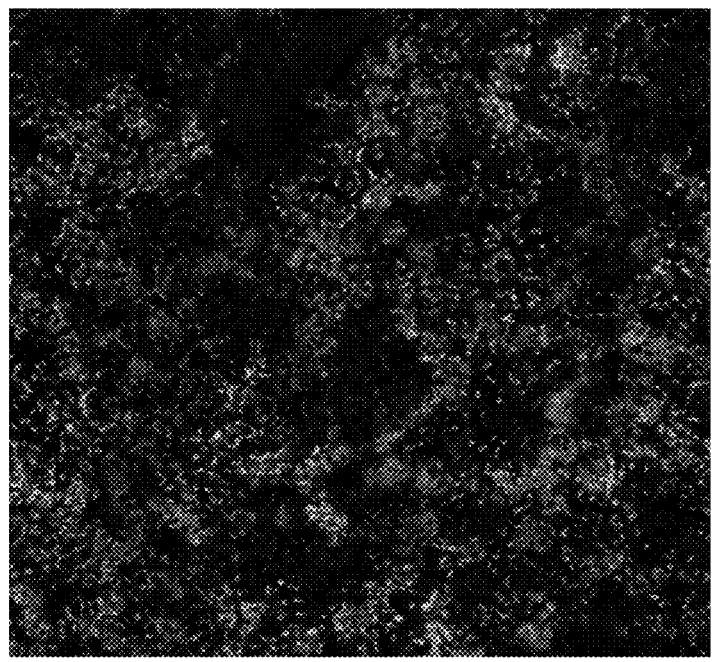
FIG. 13 provides a microscopy image of TraP11-YFP infiltrated into tobacco leaf tissues and translocated into the chloroplasts of the tobacco leaf tissues.
Figure 14:
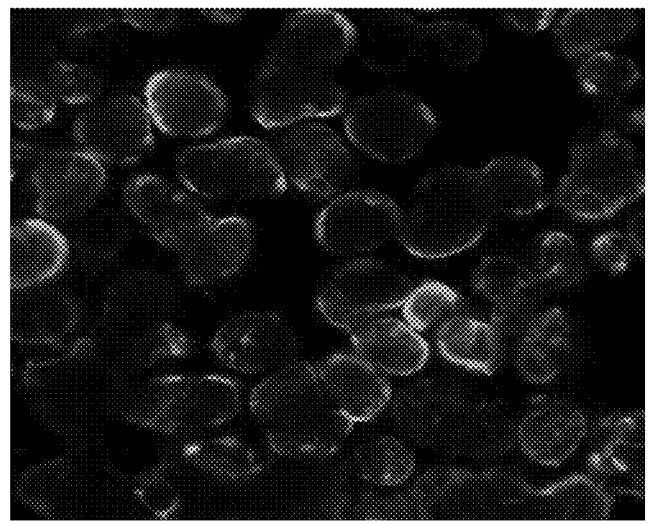
FIG. 14 provides a microscopy image of TraP17-GFP infiltrated into tobacco leaf tissues that did not translocate into the chloroplasts of the tobacco leaf tissues.
Figure 15:
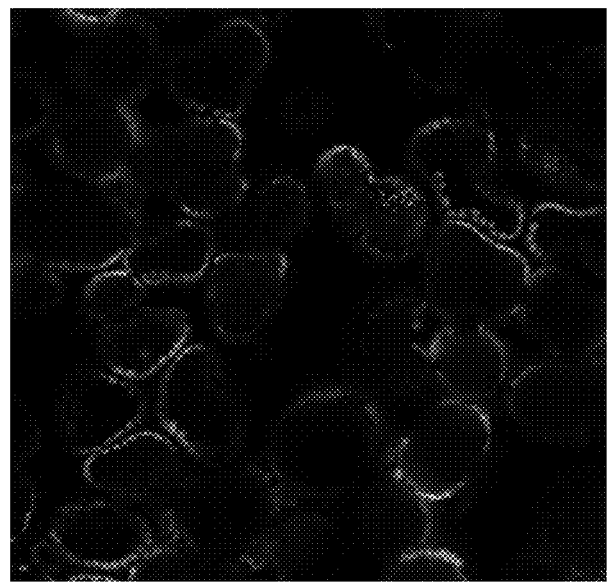
FIG. 15 provides a microscopy image of TraP18-GFP infiltrated into tobacco leaf tissues that were translocated into the chloroplasts of the tobacco leaf tissues.
Figure 16:
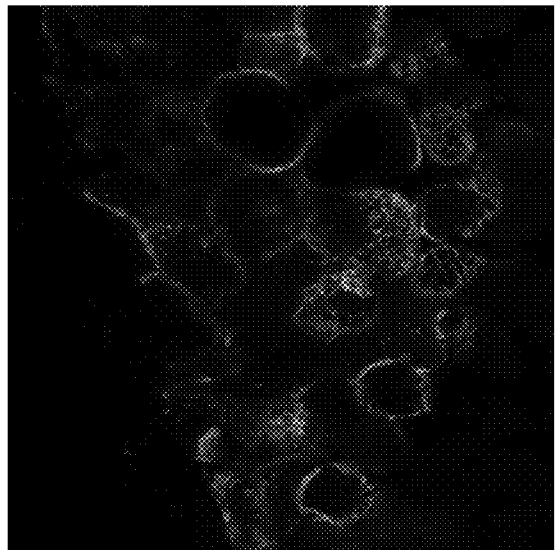
FIG. 16 provides a microscopy image of TraP19-GFP infiltrated into tobacco leaf tissues and translocated into the chloroplasts of the tobacco leaf tissues.
Figure 17:
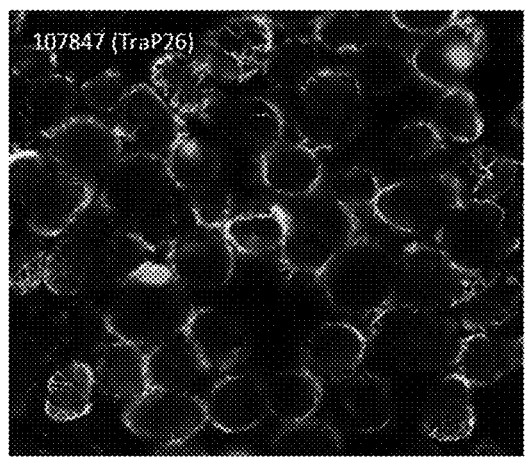
FIG. 17 provides a microscopy image of TraP26-GFP infiltrated into tobacco leaf tissue were translocated into the chloroplasts of the tobacco leaf tissues.
Figure 18:
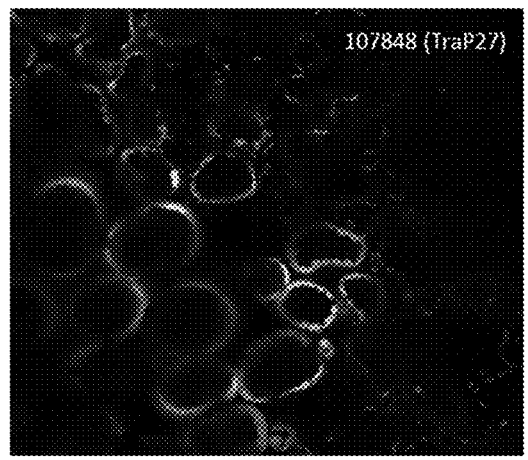
FIG. 18 provides a microscopy image of TraP27-GFP infiltrated into tobacco leaf tissues and translocated into the chloroplasts of the tobacco leaf tissues.
Figure 19:
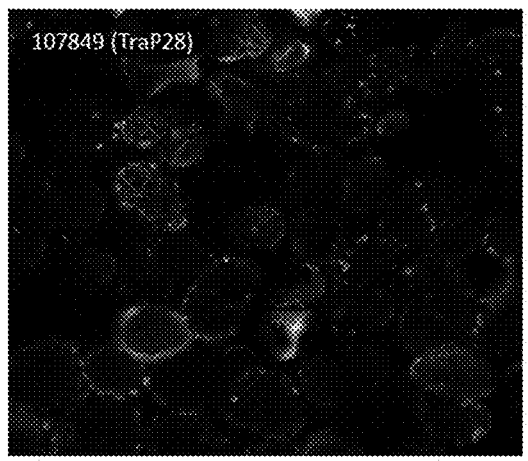
FIG. 19 provides a microscopy image of TraP28-GFP infiltrated into tobacco leaf tissues and translocated into the chloroplasts of the tobacco leaf tissues.

Example 2: Transient in Planta Testing of Chimeric Chloroplast Transit Peptide (TraP) Sequences Tobacco Transient Assay:

The above described chimeric chloroplast transit peptide sequences were initially tested via a transient in planta assay. Polynucleotide sequences which encode the TraP10 (SEQ ID NO:9), TraP11 (SEQ ID NO:10), TraP17 (SEQ ID NO:11), TraP18 (SEQ ID NO:12), TraP19 (SEQ ID NO:13), TraP26 (SEQ ID NO:14), TraP27 (SEQ ID NO:15), and TraP28 (SEQ ID NO:16), chimeric chloroplast transit peptide sequences were synthesized. A linker sequence (SEQ ID NO:17) was incorporated between the TraP sequence and the yfp coding sequence of TraP10 and TraP11. The resulting constructs contained two plant transcription units (PTU). The first PTU was comprised of the *Arabidopsis thaliana* Ubiquitin 10 promoter (AtUbi10 promoter; Callis, et al., (1990) *J. Biol. Chem.,* 265: 12486-12493), TraP-yellow fluorescent protein fusion gene (TraP-YFP; US Patent App. 2007/0298412) or the TraP-green fluorescent protein fusion gene (TraP-GFP; Sheen et al., (1995) *Plant J.,* 8(5): 777-84), and *Agrobacterium tumefaciens* ORF 23 3' untranslated region (AtuORF23 3'UTR; U.S. Pat. No. 5,428,147). The second PTU was comprised of the Cassava Vein Mosaic Virus promoter (CsVMV promoter; Verdaguer et al., (1996) *Plant Molecular Biology,* 31: 1129-1139), phosphinothricin acetyl transferase (PAT; Wohlleben et al., (1988) *Gene,* 70: 25-37) or DSM-II (International Patent App. 2008070845), and *Agrobacterium tumefaciens* ORF 1 3' untranslated region (AtuORF1 3'UTR; Huang et al., (1990) *J. Bacteriol.,* 172: 1814-1822). Construct pDAB101979 contains the TraP10 chimeric chloroplast transit peptide (FIG. 3). Construct pDAB101980 contains the TraP11 chimeric chloroplast transit peptide (FIG. 4). Construct pDAB107634 contains the TraP17 chimeric chloroplast transit peptide (FIG. 5). Construct pDAB107635 contains the TraP18 chimeric chloroplast transit peptide (FIG. 6). Construct pDAB107636 contains the TraP19 chimeric chloroplast transit peptide (FIG. 7). Construct pDAB109847 contains the TraP26 chimeric chloroplast transit peptide (FIG. 8). Construct pDAB109848 contains the TraP27 chimeric chloroplast transit peptide (FIG. 9). Construct pDAB109849 contains the TraP28 chimeric chloroplast transit peptide (FIG. 10). A control plasmid, pDAB101908, which did not contain a chloroplast transit peptide sequence upstream of the yfp gene was built and included in the studies (FIG. 11). The constructs were confirmed via restriction enzyme digestion and sequencing. Finally, the constructs were transformed into *Agrobacterium tumefaciens* and stored as glycerol stocks.

From an *Agrobacterium* glycerol stock, a loop full of frozen culture was inoculated into 2 ml of Yeast-extract Peptone Dextrose (100 µg/ml spectinomycin) in a 14 ml sterile tube. The inoculated media was incubated at 28° C. overnight with shaking at 200 rpm. The following day about 100 μl of the culture was used to inoculate 25 ml of YPD (100 μg/ml spectinomycin) in a 125 ml sterile tri-baffled flask, and incubated overnight at 28° C. overnight with shaking at 200 rpm. The following day the cultures were diluted to an $OD_{600}$ of 0.5 in sterile $ddH_2O$ (pH 8.0). The diluted *Agrobacterium* strain was mixed with a second *Agrobacterium* strain containing the P19 helper protein at a ratio of 1:1. The culture were used for tobacco leaf infiltration via the Voinnet method. Voinnet O, Rivas S, Mestre P, and Baulcombe D, (2003) An enhanced transient expression system in plants based on suppression of gene silencing by the p19 protein of tomato bushy stunt virus. *The Plant Journal*, 33: 949-956. Infiltrated tobacco plants were placed in a Conviron™ set at 16 hr of light at 24° C. for at least three days until being assayed.

Microscopy Results:

*Agrobacterium*-infiltrated tobacco leaves were severed from the plant, and placed into a petri-dish with water to prevent dehydration. The infiltrated tobacco leaves were observed under blue light excitation with long-pass filter glasses held in place using a Dark Reader Hand Lamp™ (Clare Chemical Research Co.; Dolores, Colo.) to identify undamaged areas of the leaf that were successfully expressing the YFP or GFP reporter proteins. Specifically identified leaf areas were dissected from the leaf and mounted in water for imaging by confocal microscopy (Leica TCS-SP5 AOBS™; Buffalo Grove, Ill.). The YFP was excited by a 514 nm laser line, using a multi-line argon-ion laser. The GFP was excited by a 488 nm laser line, using a multi-line argon-ion laser. The width of the detection slits was adjusted using a non-expressing (dark) control leaf sample to exclude background leaf autofluoresence. Chlorophyll autofluorescence was simultaneously collected in a second channel for direct comparison to the fluorescent reporter protein signal for determination of chloroplastic localization.

Figure 20:
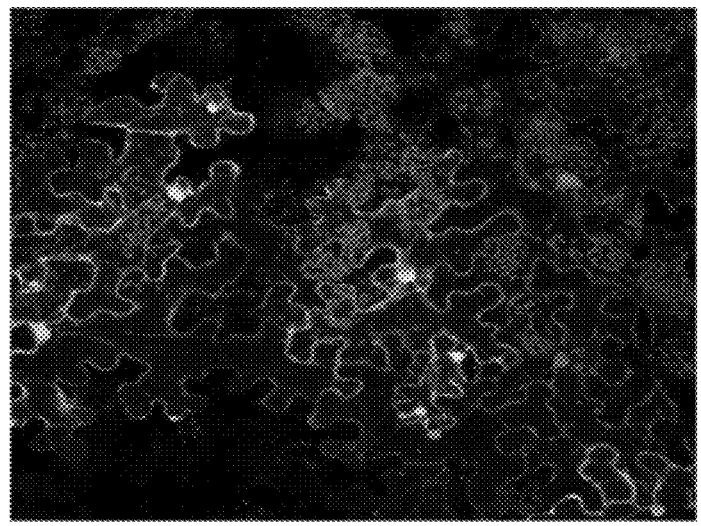
FIG. 20 provides a microscopy image of non-targeted YFP controls that were infiltrated into tobacco leaf tissues and were not incorporated into the chloroplasts of the tobacco leaf tissues.

The microscopy imaging results indicated that the YFP or GFP fluorescent protein comprising the TraP chloroplast transit peptide (TraP10, TraP11, TraP18, TraP19, TraP26, TraP27, and TraP28) accumulated within the chloroplasts located in the cytoplasm of the tobacco cells as compared to the control YFP fluorescent proteins which did not translocate into the chloroplasts of the cytoplasm of the tobacco cells (FIG. 12 to FIG. 19). It should be noted that the TraP17 transit peptide did not translocate YFP fluorescent proteins into the chloroplasts of tobacco, but the TraP17 transit peptide did translocate YFP fluorescent proteins into the chroroplasts of maize. These microscopy imaging results suggest that the translocation of the YFP protein into the chloroplast was a result of the TraP chloroplast transit peptide. As shown in the microscopy figures, the YFP fluorescence signal is localized in the chloroplasts which also fluoresce red due to auto-fluorescence under the microscopy imaging conditions. Comparatively, FIG. 20 provides a microscopy image of tobacco leaf tissue infiltrated with the control construct pDAB101908 that does not contain a chloroplast transit peptide. The chloroplasts in this image only fluoresce red due to auto-fluorescence under the microscopy imaging conditions, and are devoid of any YFP fluorescence signal that is exhibited in the TraP infiltrated tobacco cells. Rather, the YFP fluorescence signal in the control tobacco plant cells is expressed diffusely throughout the cytoplasm of the tobacco plant cells.

Maize Protoplast Transient Assay:

Seed of *Zea mays* c.v. B104 were surface sterilized by shaking vigorously in 50% Clorox™ (3% sodium hypochlorite), containing 2-3 drops of Tween® 20, for about 20 minutes. The seeds were rinsed thoroughly with sterile distilled water. The sterile seed were plated onto ½ MS medium in Phytatrays or similar type boxes, and allowed to grow in the dark (28° C.) for 12 to 20 days. A maize protoplast transient assay was used to obtain and transfect maize protoplasts from leaves of *Zea mays* c.v. B104. This maize protoplast assay is a modification of the system described by Yoo, S.-D., Cho, Y.-H., and Sheen, J., (2007), *Arabidopsis* Mesophyll Protoplasts: A Versitile Cell System for Transient Gene Expression Analysis, *Nature Protocols*, 2: 1565-1572. The solutions were prepared as described by Yoo et. al., (2007), with the exception that the mannitol concentration used for the following experiments was change to 0.6 M.

Transfection of 100 to 500 μl of protoplasts ($1-5\times10^5$ cells) was completed by adding the protoplasts to a 2 ml microfuge tube containing about 40 μg of plasmid DNA, at room temperature. The volume of DNA was preferably kept to about 10% of the protoplast volume. The protoplasts and DNA were occasionally mixed during a 5 minute incubation period. An equal volume of PEG solution was slowly added to the protoplasts and DNA, 2 drops at a time with mixing in between the addition of the drops of PEG solution. The tubes were allowed to incubate for about 10 minutes with occasional gentle mixing. Next, 1 ml of W5+ solution was added and mixed by inverting the tube several times. The tube(s) were centrifuged for 5 minutes at 75× g at a temperature of 4° C. Finally, the supernatant was removed and the pellet was resuspended in 1 ml of WI solution and the protoplasts were placed into a small petri plate (35×10 mm) or into 6-well multiwell plates and incubated overnight in the dark at room temperature. Fluorescence of GFP was viewed by microscopy after 12 hours of incubation. The microscopy conditions similar to those previously described were used for the imaging.

Figure 21:
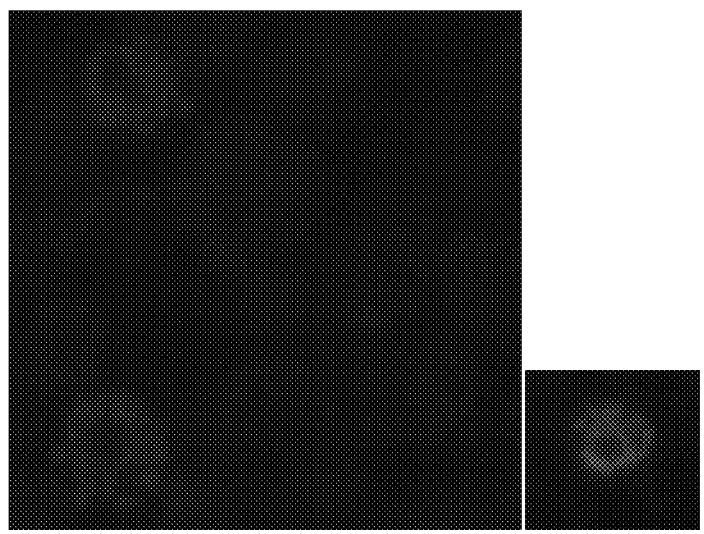
FIG. 21 provides a microscopy image of TraP17-GFP transformed into maize protoplasts and translocated into the chloroplasts of the maize protoplasts.
Figure 22:
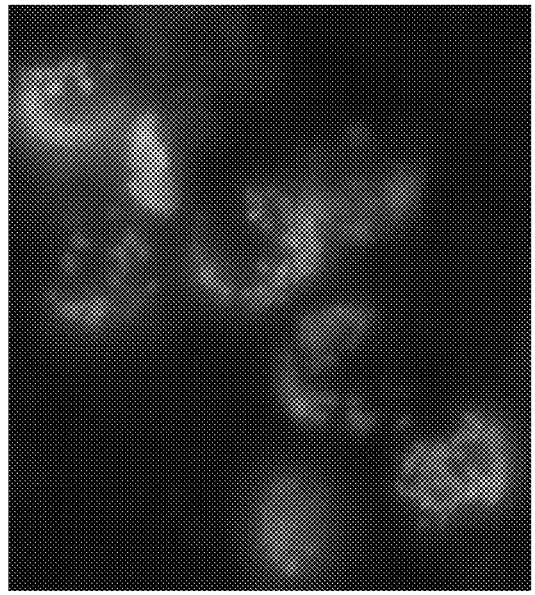
FIG. 22 provides a microscopy image of TraP18-GFP transformed into maize protoplasts and translocated into the chloroplasts of the maize protoplasts.
Figure 23:
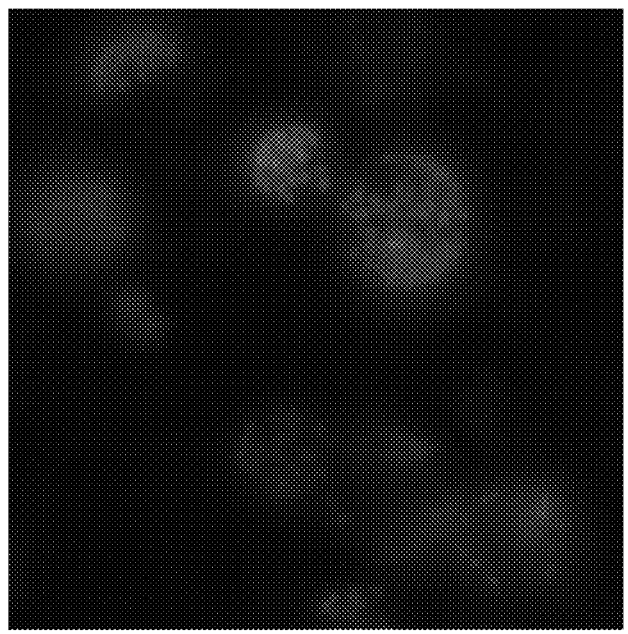
FIG. 23 provides a microscopy image of TraP19-GFP transformed into maize protoplasts and translocated into the chloroplasts of the maize protoplasts.
Figure 24:
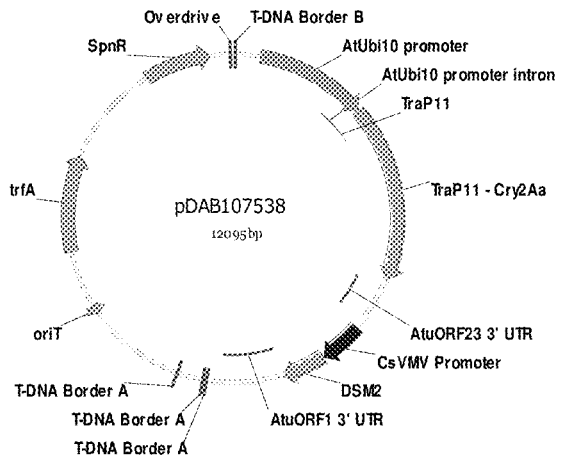
FIG. 24 provides a plasmid map of pDAB107538.
Figure 25:
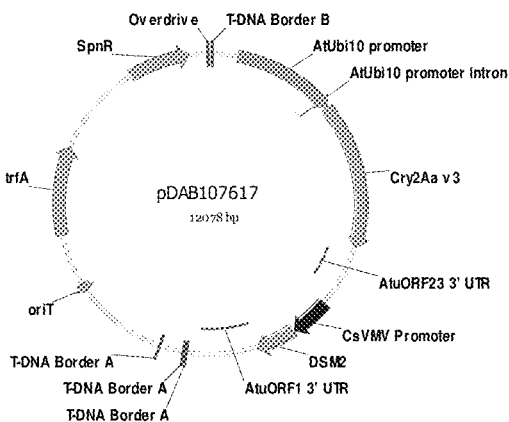
FIG. 25 provides a plasmid map of pDAB107617.
Figure 26:
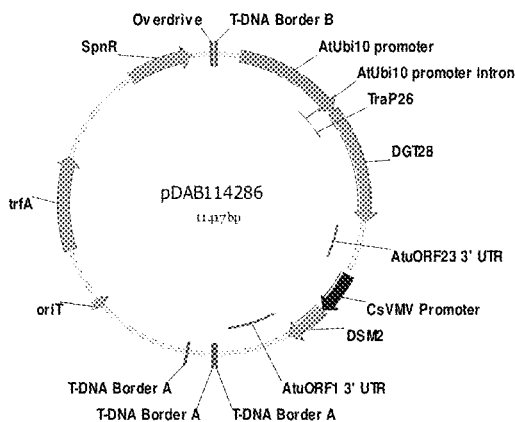
FIG. 26 provides a plasmid map of pDAB114286.
Figure 27:
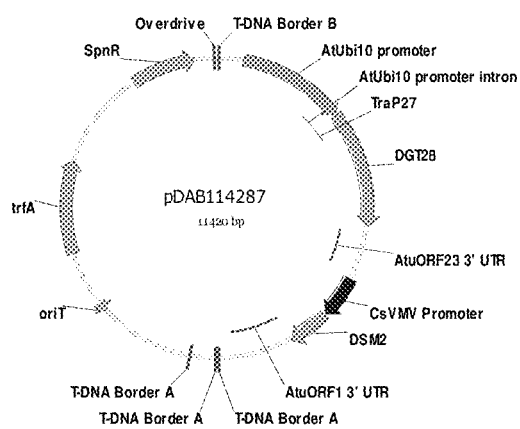
FIG. 27 provides a plasmid map of pDAB114287.

The microscopy imaging results indicated that the GFP fluorescent protein comprising a chimeric chloroplast transit peptide of TraP17, TraP18, or Trap19 accumulated within the chloroplasts located in the cytoplasm of the maize cells as compared to the control GFP fluorescent proteins which did not translocate into the chloroplasts of the cytoplasm of the maize cells (FIG. 21 to FIG. 23). These microscopy imaging results suggest that the translocation of the GFP protein into the chloroplast was a result of the TraP chimeric chloroplast transit peptide.

Western Blot Results:

Samples of the infiltrated tobacco plants were assayed via Western blotting. Leaf punches were collected and subjected to bead-milling. About 100-200 mg of leaf material was mixed with 2 BBs (Daisy; Rogers, Ark.) and 500 ml of PBST for 3 minutes in a Kleco™ bead mill. The samples were then spun down in a centrifuge at 14,000× g at 4° C. The supernatant was removed and either analyzed directly via Western blot or immunoprecipitated. The immunoprecipitations were performed using the Pierce Direct IP Kit™ (Thermo Scientific; Rockford, Ill.) following the manufacturer's protocol. Approximately, 50 μg of anti-YFP or anti-GFP was bound to the resin. The samples were incubated with the resin overnight at 4° C. Next, the samples were washed and eluted the following morning and prepped for analysis by combining equal volumes of 2×8M Urea sample buffer and then boiling the samples for 5 minutes. The boiled samples were run on a 4-12% SDS-Bis Tris gel in MOPS buffer for 40 minutes. The gel was then blotted using the Invitrogen iBlot™ (Life Technologies; Carlsbad, Calif.) following the manufacturer's protocol. The blotted membrane was blocked for 10 minutes using 5% non-fat dry milk in PBS-Tween® solution. The membrane was probed with the primary antibody (monoclonal anti-GFP or anti-YFP in rabbit) used at a 1:1000 dilution in the 5% non-fat dry milk in PBS-Tween® solution for 1 hour. Next, the membrane was rinsed three times for five minutes with PBS-Tween® to remove all unbound primary antibody. The membrane was probed with a secondary monoclonal anti-rabbit in goat antibody (Life Technologies) used at a 1:1000 dilution, for 60 minutes. The membrane was washed as previously described and developed by adding Themo BCIP/NBT™ substrate. The colormetric substrate was allowed to develop for 5-10 minutes and then the blots were rinsed with water before being dried.

The Western blot results indicated that the YFP or GFP protein was expressed in the infiltrated tobacco cells for all of the constructs tested. All of infiltrated tobacco plant leaf tissues expressed the YFP or GFP protein as indicated by the presence of a protein band which reacted to the YFP or GFP antibodies and was equivalent in size to the YFP or GFP protein band obtained from tobacco plant leaf tissue infiltrated with the YFP or GFP control construct. Moreover, these results indicated that the TraP chimeric chloroplast transit peptides (TraP10, TraP11, TraP18, TraP19, TraP26, TraP27, and TraP28) were processed and cleaved from the YFP or GFP protein. The TraP-YFP or GFP constructs express a pre-processed protein band that is larger in molecular weight than the control YFP or GFP protein. The presence of bands on the Western blot which are equivalent in size to the control YFP or GFP indicate that the TraP chloroplast transit peptide sequences (TraP10, TraP11, TraP18, TraP19, TraP26, TraP27, and TraP28) were processed, thereby reducing the size of the YFP or GFP to a molecular weight size which is equivalent to the YFP or GFP control.

Example 3: Chimeric Chloroplast Transit Peptide (TraP) Sequences for Expression of Insect Tolerant Transgenes in *Arabidopsis*

Cry2Aa:

The effectiveness of the TraP11 chimeric chloroplast transit peptides on Cry2Aa protein expression in *Arabidopsis thaliana* was assessed. Transgenic *Arabidopsis* plants which contained TraP11 chimeric chloroplast transit peptides fused to the Cry2Aa protein were assayed for insect tolerance to soybean looper (SBL) and tobacco budworm (TBW).

The TraP11 chimeric chloroplast transit peptide sequence was cloned into a plant expression construct pDAB107538 (FIG. 24) and tested in *Arabidopsis*. A new version of a polynucleotide sequence which encodes the Trap11 (SEQ ID NO:18) chimeric chloroplast transit peptide sequences was synthesized and incorporated into the plasmid construct. The resulting construct contained two plant transcription units (PTU). The first PTU was comprised of the *Arabidopsis thaliana* Ubiquitin 10 promoter (AtUbi10 promoter; Callis, et al., (1990) *J. Biol. Chem.,* 265: 12486-12493), TraP11-cry2Aa fusion gene (Cry2Aa; SEQ ID NO:19), and *Agrobacterium tumefaciens* ORF 23 3' untranslated region (AtuORF23 3'UTR; U.S. Pat. No. 5,428,147). The second PTU was comprised of the Cassava Vein Mosaic Virus promoter (CsVMV promoter; Verdaguer et al., (1996) *Plant Molecular Biology,* 31:1129-1139), dsm-2 gene (DSM2; U.S. Patent Application No. 2011/0107455), and *Agrobacterium tumefaciens* ORF 1 3' untranslated region (AtuORF1 3'UTR; Huang et al., (1990) *J. Bacteriol.,* 172:1814-1822). Construct pDAB107538 contains the TraP11 chimeric chloroplast transit peptide. A control plasmid, 107617, which did not contain a chloroplast transit peptide sequence upstream of the cry2Aa gene was built and included in the studies (FIG. 25). The constructs were confirmed via restriction enzyme digestion and sequencing. Finally, the constructs were transformed into *Agrobacterium tumefaciens* and stored as glycerol stocks.

The pDAB107538 construct was transformed into *Arabidopsis thaliana* via *Agrobacterium tumefaciens* mediated plant transformation. Briefly, 12 to 15 *Arabidopsis thaliana* plants (Columbia ecotype, Col-0) were grown in 4" pots in a green house with light intensity of 250 μmol/$m^2$, 25° C., 18/6 hours of light/dark. Primary flower stems were trimmed one week before transformation. *Agrobacterium* inoculums were prepared by incubating 10 μl of recombinant *Agrobacterium* glycerol stocks in 100 ml LB broth (100 mg/L Spectinomycin, 50 mg/L Kanamycin) at 28° C. with shaking at 225 rpm for 72 hours. A quantity of *Agrobacterium* cultures was measured with a spectrometer and when the cells reached an OD 600 of 0.8 the cells were harvested by centrifugation. Next the cells were resuspended into 3-4 volumes of 5% sucrose and 0.04% Silwet-L77™ and 10 μg/L benzamino purine (BA) infiltration medium. The above-ground parts of plant were dipped into the *Agrobacterium* solution for 5-10 minutes, with gentle agitation. The plants were then transferred to the greenhouse for normal growth with regular watering and fertilizing until seed set.

About 200 mg(s) of bulked $T_1$ seeds were planted evenly in selection trays (10.5"×21"×1" germination trays T.O. Plastics Inc., Clearwater, Minn.). Seedlings were sprayed with a 0.20% solution (20 μl/10 mL $dH_2O$) of glufosinate herbicide (Liberty™) in a spray volume of 10 ml/tray (703 L/ha) 5 days post-sowing and again at 10 days post-sowing using a DeVilbiss compressed air spray tip. Between 4 to 7 days after the second application of glufosinate, herbicide tolerant plants were identified and transplanted for $T_2$ seed production. The resulting $T_2$ seeds were used in the studies described below.

A small aliquot of $T_2$ seed (approx. 100-200 seeds) for each event were suspended in 40 mls of 0.1% agarose solution and cold stratified at 4° C. for 24 hrs. The stratified seeds were then sown by pipetting 10 ml of seed onto the surface of four flats in a propagation flat. The flats were filled with Sunshine #5 soil Media™ (Sun Gro; Bellevue, Wash.) and lightly covered with fine vermiculite. The trays were saturated in Hoagland's fertilizer prior to sowing and as needed afterward. After sowing, humidity domes were used to cover the trays and they were then placed into a Conviron™ growth chamber set at 24° C. with a 16 hr photo period. Incandescent and fluorescent lights provided a light level of 200 PAR. After 5 days the seeds germinated and the domes were removed. The first herbicide selection of transformants was on day 6 and the second on day 10. Liberty™ herbicide (a.i. glufosinate-ammonium) was applied using a DeVilbiss atomizer hand sprayer at a rate of 200 g ai/ha to remove nulls. Roughly 25% of the plants were nulls as expected. A row of wild type checks were also included in the selection and they had 100% mortality after two herbicide applications. At 14 days the plants were ready for transplanting. Twelve plants were taken from each event for bio-assay and transplanted into 3" pots filled with Sunshine No. 5 soil that had a light covering of fine vermiculite. The flats were presoaked with Hoagland's fertilizer prior to transplant and afterward as needed. The transplants were propagated in a non-air conditioned green house set at 25° C. with 14 hours of supplemental light. Silique development was inhibited by trimming with scissors and thus created more plant tissue for testing. Plants were ready for DNA sampling at 16-18 days and ready for bio-assay at about 23 days. The putative transgenic plants were screened using molecular confirmation assays and identified events were advanced for protein analysis and bioassay results.

The transformed plants generally showed a healthy phenotype although some plants were smaller in size when visually compared with the wild type plants. Analysis of gene copy number for each *Arabidopsis* construct showed comparable insertion results for all the constructs, with about 50% of the plants having ≥3 copies of the cry2Aa gene of interest and about 50% having 1-2 copies of the gene.

The Cry2Aa protein expression levels of the $T_1$ *Arabidopsis* events ranged widely. Protein detection was completed using an ELISA assay to quantitate Cry2Aa protein expression. Generally, the protein expression levels correlated with the copy number of T-strand insert for each event. High T-strand copy number events (e.g. >3 insertion events) generally produced higher mean protein expression levels than the low T-strand copy number events for both sets of *Arabidopsis* transformation events (e.g. pDAB107617 events expressing Cry2Aa without a TraP and pDAB107538 events expressing Cry2Aa with a TraP 11 chimeric chloroplast transit peptide).

The $T_2$ generation of *Arabidopsis* plants expressed Cry2Aa protein values that were reduced in comparison to expression values of the $T_1$ *Arabidopsis* plants. These results indicated that protein expression was variable among each set of events. Average protein expression levels obtained from the homozygous events was greater than the average protein expression levels obtained from the hemizygous events for all of the plant events tested (e.g., events without a TraP [pDAB107617] and with TraP11 [pDAB107538]). The *Arabidopsis* events which contained more than two copies of a T-strand insert had higher levels of expression than *Arabidopsis* events which contained only a single copy. Despite the decrease in protein expression levels from the $T_1$ to the $T_2$ generation, the incorporation of the TraP11 chimeric chloroplast transit peptide within the constructs resulted in transgenic *Arabidopsis* events which expressed the Cry2Aa protein.

Both sets of $T_1$ *Arabidopsis* events were tested in insect bioassay experiments. In general, high copy number events which expressed greater amounts of Cry2Aa protein resulted in lower amounts of leaf damage as compared to low copy number events. There was a correlation between protein expression and leaf protection against both SBL and TBW for *Arabidopsis* events expressing Cry2Aa without a TraP ($r^2$=0.49 [SBL], 0.23 [TBW]), and for *Arabidopsis* events expressing Cry2Aa with TraP11 ($r^2$=0.75 [SBL], 0.17 [TBW]). Resultantly, an increase in protein expression caused significant protection against leaf damage (Pr<0.05).

*Arabidopsis* plants were protected from SBL damage in both the TraP11 and non TraP *Arabidopsis* events. Expression of Cry2Aa with and without a TraP11 resulted in lower than 30% leaf damage with minimum protein expression of about 1.0 ng/cm$^2$ for TraP11:Cry2Aa events and about 1.5 ng/cm$^2$ for Cry2Aa events without a TraP. Assessments of *Arabidopsis* event expression of Cry2Aa with and without TraP11 resulted in lower than 20% leaf damage, with minimum protein expression of about 1.1 ng/cm$^2$ for TraP11 *Arabidopsis* events and about 2.0-2.5 ng/cm$^2$ for non-TraP *Arabidopsis* events.

*Arabidopsis* plants were protected from TBW damage by both the TraP11 and non TraP *Arabidopsis* events. The TBW insects were more sensitive to Cry2Aa protein than the SBL insects when fed with plant material obtained from the *Arabidopsis* events. Protein concentrations as low as about 1.0 and 1.5 ng/cm$^2$ of Cry2Aa resulted in less than 30% leaf damage when the Cry2Aa protein was expressed in combination with TraP11 and without a TraP, respectively. At the 20% leaf damage cut-off point, leaf protection from TraP11 *Arabidopsis* events resulted from levels of about 1.1 ng/cm$^2$ of Cry2Aa protein while 2.0-2.5 ng/cm$^2$ of expressed Cry2Aa protein was required from the *Arabidopsis* events which did not possess a TraP.

The TraP11 chimeric chloroplast transit peptides did not reduced the effectiveness of Cry2Aa protein expression in *Arabidopsis thaliana*. Transgenic *Arabidopsis* plants which contained the TraP11 chimeric chloroplast transit peptides fused to the Cry2Aa protein expressed high levels of the Cry2Aa protein which provided insect tolerance to soybean looper (SBL) and tobacco budworm (TBW).

Example 4: Chimeric Chloroplast Transit Peptide (TraP) Sequences for Expression of Herbicide Tolerant Transgenes in *Arabidopsis*

DGT28:

The effectiveness of the TraP26 and TraP27 chimeric chloroplast transit peptides on DGT28 (PCT/US2013/024488) protein expression in *Arabidopsis thaliana* was assessed. Transgenic *Arabidopsis* plants which contained either TraP26 or TraP27 chimeric chloroplast transit peptides fused to the DGT28 protein were assayed for herbicide tolerance to applications of glyphosate.

The TraP26 chimeric chloroplast transit peptide sequence was cloned into a plant expression construct pDAB114286 (FIG. 26) and tested in *Arabidopsis*. The resulting construct contained two plant transcription units (PTU). The first PTU was comprised of the *Arabidopsis thaliana* Ubiquitin 10 promoter (AtUbi10 promoter; Callis, et al., (1990) *J. Biol. Chem.,* 265: 12486-12493), TraP26-dgt28 fusion gene (TraP26-DGT28; SEQ ID NO:27), and *Agrobacterium tumefaciens* ORF 23 3' untranslated region (AtuORF23 3'UTR; U.S. Pat. No. 5,428,147). The second PTU was comprised of the Cassava Vein Mosaic Virus promoter (CsVMV promoter; Verdaguer et al., (1996) *Plant Molecular Biology,* 31:1129-1139), dsm-2 gene (DSM2; U.S. Patent Application No. 2011/0107455), and *Agrobacterium tumefaciens* ORF 1 3' untranslated region (AtuORF1 3'UTR; Huang et al., (1990) *J. Bacteriol.,* 172:1814-1822). Construct pDAB114286 contains the TraP26 chimeric chloroplast transit peptide.

The TraP27 chimeric chloroplast transit peptide sequence was cloned into a plant expression construct pDAB114287 (FIG. 27) and tested in *Arabidopsis*. The resulting construct contained two plant transcription units (PTU). The first PTU was comprised of the *Arabidopsis thaliana* Ubiquitin 10 promoter (AtUbi10 promoter; Callis, et al., (1990) *J. Biol. Chem.,* 265: 12486-12493), TraP27-dgt28 fusion gene (TraP27-DGT28; SEQ ID NO:28), and *Agrobacterium tumefaciens* ORF 23 3' untranslated region (AtuORF23 3'UTR; U.S. Pat. No. 5,428,147). The second PTU was comprised of the Cassava Vein Mosaic Virus promoter (CsVMV promoter; Verdaguer et al., (1996) *Plant Molecular Biology,* 31:1129-1139), dsm-2 gene (DSM2; U.S. Patent Application No. 2011/0107455), and *Agrobacterium tumefaciens* ORF 1 3' untranslated region (AtuORF1 3'UTR; Huang et al., (1990) *J. Bacteriol.,* 172:1814-1822). Construct pDAB114287 contains the TraP27 chimeric chloroplast transit peptide.

Both of the constructs were confirmed via restriction enzyme digestion and sequencing. The constructs were transformed into *Agrobacterium tumefaciens* and stored as glycerol stocks. Finally, the constructs were transformed into *Arabidopsis thaliana* via the *Agrobacterium*-transformation method described above.

Plant Transformation:

Freshly harvested transgenic $T_1$ seeds containing the dgt-28 and DSM-2 expression cassettes were allowed to dry for 7 days at room temperature. $T_1$ seeds were sown in 26.5×51 cm germination trays, each receiving a 200 mg aliquot of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 Soil™ was covered with fine vermiculite and subirrigated with Hoagland's solution until wet, then allowed to gravity drain. Each 40 ml aliquot of stratified seed was sown evenly onto the vermiculite with a pipette and covered with humidity domes for 4-5 days. Domes were removed one day prior to initial transformant selection using glufosinate postemergence spray (selecting for the co-transformed dsm-2 gene).

Seven days after planting (DAP) and again 11 DAP, $T_1$ plants (cotyledon and 2-4-1f stage, respectively) were sprayed with a 0.2% solution of Liberty™ herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360™). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 h light:10 h dark, minimum 500 μE/m²s¹ natural+supplemental light). Molecular confirmation analysis was completed on the surviving $T_1$ plants to confirm that the glyphosate tolerance gene had stably integrated into the genome of the plants Molecular Confirmation:

The presence of the dgt-28 and dsm-2 transgenes within the genome of *Arabidopsis* plants that were transformed with pDAB114286 and pDAB114287 were confirmed. The presence of these polynucleotide sequences were confirmed via hydrolysis probe, gene expression cassette PCR (also described as plant transcription unit PCR; PTU PCR), Western blot, and ELISA analysis.

The $T_1$ *Arabidopsis* plants were initially screened to confirm the presence of the dgt-28 and dsm-2 transgene and AtUbi10 promoter. Events were screened via gene expression cassette PCR to determine whether the dgt expression cassette completely integrated into the plant genomes without rearrangement. Next, the $T_1$ *Arabidopsis* plants were screened via a hydrolysis probe assay, analogous to TAQMAN™. The data generated from these studies were used to determine the transgene copy number and identify select *Arabidopsis* events for self fertilization and advancement to the $T_2$ generation. Copy numbers were determined in the $T_1$ *Arabidopsis* plants using the hydrolysis probe assay described below. Plants with varying numbers of transgenes were identified and advanced for subsequent glyphosate tolerance studies.

Tissue samples were collected in 96-well plates and lyophilized for 2 days. Maceration of fresh tissue was performed with a KLECO™ tissue pulverizer and tungsten beads (Environ Metal INC., Sweet Home, Oreg.). Following tissue maceration, the genomic DNA was isolated in high-throughput format using the Biosprint 96 Plant Kit™ (Qiagen, Germantown, Md.) according to the manufacturer's suggested protocol. Post isolation, gDNA was diluted in a standard 1:3 dilution. Transgene copy number determination by hydrolysis probe assay was performed by real-time PCR using the LIGHTCYCLER®480 system (Roche Applied Science, Indianapolis, Ind.). Assays were designed for dsm-2, AtUbi10 and the internal reference gene, TAFII15 (Genbank ID: NC 003075; Duarte et al., *BMC Evol. Biol.*, 10:61).

For amplification, LIGHTCYCLER®480 Probes Master mix (Roche Applied Science, Indianapolis, Ind.) was prepared at a 1× final concentration in a 10 μL volume multiplex reaction containing 0.1 μM of each primer for dsm-2 and AtUbi10, 0.4 μM of each primer for TAFII15 and 0.2 μM of each probe (Table 1). A two-step amplification reaction was performed with an extension at 60° C. for 40 seconds with fluorescence acquisition. All samples were run and the averaged cycle threshold (Ct) values were used for analysis of each sample. Analysis of real time PCR data was performed using LightCycler software release 1.5™ using the relative quant module and is based on the ΔΔCt method. For this, a sample of genomic DNA from a single copy calibrator and known 2 copy check were included in each run. The copy number results of the hydrolysis probe screen were determined for the $T_1$ transgenic *Arabidopsis* plants.

TABLE 1

Primer and probe Information for hydrolysis probe assay of dsm-2, AtUbi10 and internal reference gene (TAFII15).

| Primer Name | Sequence |
|---|---|
| DSM2A (SEQ ID NO: 29) | 5' AGCCACATCCCAGTAACGA 3' |
| DSM2S (SEQ ID NO: 30) | 5' CCTCCCTCTTTGACGCC 3' |
| DSM2 Cy5 probe (SEQ ID NO: 31) | 5' CAGCCCAATGAGGCATCAGC 3' |
| AtUbi10v2Set5-F (SEQ ID NO: 32) | 5' CTTCACCGCCTTAGCTTTCT 3' |
| AtUbi10v2Set5-R (SEQ ID NO: 33) | 5' GTGAAGAAGAAGCTTTGGGTATTG 3' |
| AtUbi10v2Set5-FAM (SEQ ID NO: 34) | 5' CGTGACCTAGTCGTCCTCGTCTTT 3' |
| TAFFY-HEX probe (SEQ ID NO: 35) | 5' AGAGAAGTTTCGACGGATTTCGGGC 3' |
| TAFII15-F (SEQ ID NO: 36) | 5' GAGGATTAGGGTTTTCAACGGAG 3' |
| TAFII15-R (SEQ ID NO: 37) | 5' GAGAATTGAGCTGAGACGAGG 3' |

A Western blot was completed to detect the expressed DGT-28 protein in leaf samples obtained from transgenic *Arabidopsis thaliana* plants. Conventional electrophoresis and blotting methods were used with Irivitrogen™ devices and basic reagents. Gallagher S, Winston S, Fuller S, Hurrell J, "Immunoblotting and Immunodetection" Current Protocols in Immunology 8.10.1-8.10.28, November 2008. Positive transgenic events which expressed the DGT-28 protein were detected using a rabbit anti-DGT-28 antibody as the primary antibody with an anti-rabbit fluorescence (Cy3) detection system. Production of an intact DGT-28 protein via Western blot indicated that the transgenic plants which were assayed expressed the DGT-28 protein at the appropriate molecular weight. The Western blots were observed to contain two protein bands of differing molecular weights. It was hypothesized that the two bands are comprised of a first lower molecular weight processed DGT-28 protein that resulted from cleavage of the chloroplast transit peptide from the dgt-28 transgene and a second larger, full length TraP::DGT-28 protein that was not processed and did not result in cleavage of the chloroplast transit peptide sequence.

ELISA assays were used to confirm that the transgenic events identified using the Western blot, and qPCR assays expressed the transgenes. Two leaf samples that were 6 mm in diameter were collected and placed in a 96 well cluster tube rack. Next, two Daisy™ steel BB's and 200 µl of extraction buffer (50 mM HEPES, 5.97 g/500 ml, buffer pH 7.5 with 1% Brij™ 0.5 g/500 ml, protease inhibitors 5 µl/ml) were added to each tube. The samples were milled in a Klecko™ tissue pulverizer for 3 minutes on maximum setting. Samples were centrifuged at 3,000×g for 5 minutes and 100 µl of the supernatant was transferred to an empty sample tube. Another 100 µl of extraction buffer was added to the plant sample and bead milled 3 additional minutes, centrifuged and 100 µl of this extract was combined with the first 100 µl of solution. The combined supernatants were mixed and analyzed the same day as the collection.

Monoclonal antibodies were developed for the ELISA assays. The capture antibody clone, SW4-8F11, was coated on a maxisorp plate at 2 µg/ml in PBS, and incubated overnight at 4° C. Then the plates were washed with PBS (10× stock), Tween®-20 with four well volumes of buffer. The ELISA plates were blocked with 200 µl per well of PBS (10× stock), Tween®-20, and 2% fish gelatin for two hours at room temperature. Plates were washed with PBS (10× stock) and Tween®-20 with four well volumes of buffer. Samples were prepared as described above and standard curved applied at 60 ng/ml with 2-fold dilutions to 0.94 ng/ml, in the following buffer: 50 mM HEPES, 5.97 g/500 ml, buffer pH 7.5 with 1% Brij™, 0.5 g/500 ml, protease inhibitors 5 µl/ml. Samples and standards were added at 100 µl per well for two hours at room temperature with shaking. Then the plates were washed with PBS (10× stock) and Tween®-20 with four well volumes of buffer. Detection antibody clone, SW4-18F5, conjugated to peroxidase was added to each at 100 µl per well at a concentration of 1 µg/ml and incubated for one hour at room temperature. Plates were washed with PBS (10× stock) and Tween®-20 with four well volumes of buffer. The TMB™ (Pierce) substrate was added at 100 µl per well and incubated approximately 10 minutes or until appropriate color developed. The color development was stopped with 100 µl per well of 0.4M H2SO4. The plates were read at 450 nm, using Softmax™ software. The resulting ELISA data that was obtained from simple copy $T_1$ events demonstrated a mean DGT-28 protein expression of 77 ng/cm$^2$ with a standard deviation of +/−33 ng/cm$^2$.

Glyphosate Tolerance:

The *Arabidopsis* $T_1$ transformants (from transformation with pDAB114286 or pDAB114287) were first selected from the background of untransformed seed using a glufosinate selection scheme. Three flats or 50,000 seed were analyzed for each $T_1$ construct. The selected $T_1$ plants were molecularly characterized (as described above) and events with a range of copy number were sprayed with various rates of commercial glyphosate.

Transgenic $T_1$ *Arabidopsis* plants containing the dgt-28 transgene were sprayed with differing rates of glyphosate. Elevated rates were applied in this study to determine the relative levels of resistance (420, 840, 1,680 or 3,360 g ae/ha). The typical 1× field usage rate of glyphosate is 1120 g ae/ha. The response of these plants is presented in terms of % visual injury 2 weeks after treatment (WAT). The $T_1$ *Arabidopsis* plants that were used in this study were of variable copy number for the dgt-28 transgene. The low copy dgt-28 $T_1$ *Arabidopsis* plants were self-pollinated and used to produce $T_2$ plants. Table 2 shows the comparison of dgt-28 transgenic plants, drawn to a wildtype (non-transgenic) control.

The data presented show individual plants exhibiting little or no injury (<20%), moderate injury (20-40%), or severe injury (>40%). An arithmetic mean and standard deviation is presented for each construct used for *Arabidopsis* transformation. The range in individual response is also indicated in the last column for each rate and transformation. Wildtype, non-transformed *Arabidopsis thaliana* c.v. Columbia served as a glyphosate sensitive control.

The level of plant response to the application of glyphosate varied. This variance can be attributed to the fact each plant represents an independent transformation event and thus the copy number of the gene of interest varies from plant to plant. However, the data demonstrates that dgt-28 linked with the chloroplast transit peptides sequences of TraP26 and TraP27 provide protection to glyphosate.

TABLE 2

The dgt-28 transformed $T_1$ *Arabidopsis* response to a range of glyphosate rates applied postemergence, compared to a non-transformed control. Visual % injury was recorded 14 days after application of glyphosate.

| Application Rate | % Injury Range (No. Replicates) | | | % Injury Analysis | | |
|---|---|---|---|---|---|---|
| | <20% | 20-40% | >40% | Ave | Std dev | Range (%) |
| TraP26::dgt-28 (pDAB114286) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 10.0 | 0.0 | 10 |
| 3360 g ae/ha glyphosate | 3 | 1 | 0 | 16.3 | 2.5 | 15-20 |
| TraP27::dgt-28 (pDAB114287) | | | | | | |
| 0 g ae/ha glyphosate | 4 | 0 | 0 | 0.0 | 0.0 | 0 |
| 420 g ae/ha glyphosate | 3 | 1 | 0 | 19.0 | 8.2 | 10-30 |
| 840 g ae/ha glyphosate | 3 | 1 | 0 | 15.8 | 4.3 | 10-20 |
| 1680 g ae/ha glyphosate | 1 | 3 | 0 | 18.8 | 2.5 | 15-20 |
| 3360 g ae/ha glyphosate | 0 | 4 | 0 | 25.0 | 0.0 | 25 |
| WT (non-transformed control) | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

What is claimed is:

1. A chimeric nucleic acid molecule comprising:
a nucleotide sequence that encodes a peptide of less than 73 amino acids in length, wherein the peptide is at least 95% identical to one of SEQ ID NO:1, SEQ ID NO:2, and SEQ ID NO:6, operably linked in frame to a heterologous nucleotide coding sequence of interest.

2. The chimeric nucleic acid molecule of claim 1, wherein the peptide is at least 95% identical to SEQ ID NO:1.

3. The chimeric nucleic acid molecule of claim 1, wherein the peptide is at least 95% identical to SEQ ID NO:2.

4. The chimeric nucleic acid molecule of claim 1, wherein the peptide is at least 95% identical to SEQ ID NO:6.

5. The chimeric nucleic acid molecule of claim 1, wherein the peptide is SEQ ID NO:1.

6. The chimeric nucleic acid molecule of claim 1, wherein the peptide is SEQ ID NO:2.

7. The chimeric nucleic acid molecule of claim 1, wherein the peptide is SEQ ID NO:6.

8. The chimeric nucleic acid molecule of claim 1, wherein the nucleotide coding sequence of interest is a dsm-2 coding sequence, a dgt-28 coding sequence, a Bt toxin gene coding sequence, a yfp coding sequence or a gfp coding sequence.

9. The chimeric nucleic acid molecule of claim 1, wherein the nucleotide sequence that encodes the peptide remains hybridized to one of SEQ ID NO:9, SEQ ID NO:10, and SEQ ID NO:14 after: hybridization in 5×SSC, 0.1% SDS buffer at 65° C. for 16 hours; washed twice in 2×SSC, 0.1% SDS buffer at room temperature for 15 minutes each; and washed twice in 0.5×SSC, 0.1% SDS buffer at 65° C. for 20 minutes each.

10. The chimeric nucleic acid molecule of claim 1, wherein the nucleotide sequence is operably linked to one or more regulatory sequences.

11. A chimeric polypeptide encoded by the chimeric nucleic acid molecule of claim 1 comprising the peptide and a further peptide encoded by the heterologous nucleic acid sequence of interest.

12. The chimeric polypeptide of claim 11, wherein the further peptide encoded by the nucleotide sequence of interest is targeted to a plastid in a plastid-containing cell.

13. The chimeric polypeptide of claim 12, wherein wherein the peptide is a chloroplast transit peptide that is removed when the chimeric polypeptide is imported into the plastid.

14. The chimeric polypeptide of claim 13, wherein the chimeric polypeptide comprises a chloroplast-targeted peptide that remains when the chloroplast transit peptide is removed, wherein the chloroplast-targeted peptide is encoded by the nucleotide coding sequence of interest.

15. The chimeric polypeptide of claim 11, wherein the further peptide encoded by the nucleotide coding sequence of interest is a biologically-active peptide.

16. The chimeric polypeptide of claim 11, wherein the nucleotide coding sequence of interest encodes a fluorescent peptide.

17. The chimeric polypeptide of claim 15, wherein the biologically-active peptide is an enzyme.

18. The chimeric polypeptide of claim 15, wherein the biologically-active peptide is normally expressed in a plastid of a cell wherein the biologically-active peptide is natively expressed.

19. The chimeric polypeptide of claim 15, wherein the biologically-active peptide confers a desirable agronomic trait selected from the group consisting of herbicide resistance, virus resistance, bacterial pathogen resistance, insect resistance, nematode resistance, fungal resistance, plant vigor, plant yield, temperature tolerance, soil condition tolerance, low light level tolerance, low water level tolerance, high water level tolerance, chemical environment tolerance, seed color, starch modification, amino acid synthesis, photosynthesis, synthesis of fatty acids, oil synthesis, synthesis of carotenoids, synthesis of terpenoids, synthesis of starch, and herbicide resistance.

20. The chimeric polypeptide of claim 15, wherein the biologically-active peptide is selected from the group consisting of a zeaxanthin epoxidase, a choline monooxygenase, a ferrochelatase, a omega-3 fatty acid desaturase, a glutamine synthetase, a hormone, a Bt toxin protein, and a reporter protein useful in identification of plants comprising a trait of interest.

21. The chimeric polypeptide of claim 19, wherein the biologically-active peptide is involved in herbicide resistance.

22. The chimeric polypeptide of claim 21, wherein the biologically-active peptide is selected from the group consisting of: acetolactase synthase (ALS), mutated ALS, precursor of ALS, 3-enolpyruvylshikimate-5-phosphate synthase (EPSPS), DGT-28 EPSPS, CP4 EPSPS, a class IV EPSPS, and a class III EPSPS.

23. The chimeric polypeptide of claim 19, wherein the biologically-active peptide is involved in insect resistance.

24. A plant expression vector comprising the nucleic acid molecule of claim 10.

25. A plant material comprising the chimeric nucleic acid molecule of claim 1.

26. The plant material of claim 25, wherein the plant material is selected from the group consisting of a plant cell, a plant tissue, a plant tissue culture, a callus culture, a plant part, and a whole plant.

27. The plant material of claim 26, further comprising a polypeptide comprising the peptide and a further peptide encoded by the nucleotide coding sequence of interest.

28. The plant material of claim 27, wherein the nucleotide coding sequence of interest encodes a portion of the polypeptide that is imported into a plastid in a cell of the plant material.

29. The plant material of claim 25, wherein the nucleic acid molecule is stably integrated into the genome of a cell in the plant material.

30. The plant material of claim 25, wherein the plant material is a whole plant.

31. The plant material of claim 25, wherein the plant material is from a plant selected from the group consisting of *Arabidopsis*, alfalfa, *Brassica*, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, watermelon, corn, onion, rice, sorghum, wheat, rye, millet, sugarcane, oat, triticale, switchgrass, and turfgrass.

32. A method for producing a transgenic plant material, the method comprising:
obtaining the chimeric nucleic acid molecule of claim 1; and
transforming a plant material with the nucleic acid molecule.

33. The method according to claim 32, wherein the plant material is selected from the group consisting of a plant cell, a plant tissue, a plant tissue culture, a callus culture, a plant part, and a whole plant.

34. The method according to claim 33, wherein the plant material is not a whole plant.

35. A transgenic plant material produced by the method of claim 32 comprising the chimeric nucleic acid molecule.

36. A transgenic plant material produced by the method of claim 34 comprising the chimeric nucleic acid molecule.

37. A transgenic plant regenerated from the plant material of claim 36 comprising the chimeric nucleic acid molecule.

38. A transgenic plant commodity product produced from the plant material of claim 35 comprising the chimeric nucleic acid molecule.

39. The transgenic plant material of claim 35, wherein the nucleotide coding sequence of interest encodes a biologically-active peptide.

40. The transgenic plant material of claim 39, wherein the biologically-active peptide is involved in a process selected from the group consisting of herbicide resistance, virus resistance, bacterial pathogen resistance, insect resistance, nematode resistance, fungal resistance, plant vigor, plant yield, temperature tolerance, soil condition tolerance, low light level tolerance, low water level tolerance, high water level tolerance, chemical environment tolerance, seed color, starch modification, amino acid synthesis, photosynthesis, synthesis of fatty acids, oil synthesis, synthesis of carotenoids, synthesis of terpenoids, synthesis of starch, and herbicide resistance.

41. The transgenic plant material of claim 39, wherein the biologically-active peptide is selected from the group consisting of a zeaxanthin epoxidase, a choline monooxygenase, a ferrochelatase, a omega-3 fatty acid desaturase, a glutamine synthetase, a hormone, a Bt toxin protein, and a reporter protein useful in identification of plants comprising a trait of interest.

42. The transgenic plant material of claim 40, wherein the biologically-active peptide is involved in herbicide resistance.

43. The transgenic plant material of claim 42, wherein the biologically-active peptide is selected from the group consisting of: acetolactase synthase (ALS), mutated ALS, precursors of ALS, 3-enolpyruvylshikimate-5-phosphate synthase (EPSPS), CP4 EPSPS, and a class III EPSPS.

44. The transgenic plant material of claim 42, wherein the plant material exhibits increased herbicide resistance or herbicide tolerance when compared to a wild-type plant material of the same species.

45. The plant material of claim 26, wherein the plant material is a plant cell that is incapable of regeneration to produce a plant.

46. The method according to claim 32, wherein the plant material is a plant cell that is incapable of regeneration to produce a plant.

* * * * *

SEQUENCE LISTING

<160> NUMBER OF SEQ ID NOS: 37

<210> SEQ ID NO 1
<211> LENGTH: 72
<212> TYPE: PRT
<213> ORGANISM: artificial sequence
<220> FEATURE:
<223> OTHER INFORMATION: TraP10

<400> SEQUENCE: 1

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
                20                  25                  30

Val Ser Leu Arg Pro Arg Leu Trp Gly Ala Ser Lys Ser Arg Ile Pro
            35                  40                  45

Met His Lys Asn Gly Ser Phe Met Gly Asn Phe Asn Val Gly Lys Gly
        50                  55                  60

Asn Ser Gly Val Phe Lys Val Ser
65                  70

<210> SEQ ID NO 2
<211> LENGTH: 68
<212> TYPE: PRT
<213> ORGANISM: artificial sequence
<220> FEATURE:
<223> OTHER INFORMATION: TraP11

<400> SEQUENCE: 2

Met Ala Gln Val Ser Arg Val His Asn Leu Ala Gln Ser Thr Gln Ile
1               5                   10                  15

Phe Gly His Ser Ser Asn Ser Asn Lys Leu Lys Ser Val Asn Ser Val
                20                  25                  30

Ser Leu Lys Thr His Gln Pro Arg Ala Ser Ser Trp Gly Leu Lys Lys
            35                  40                  45

Ser Gly Thr Met Leu Asn Gly Ser Val Ile Arg Pro Val Lys Val Thr
        50                  55                  60

Ala Ser Val Ser
65

<210> SEQ ID NO 3
<211> LENGTH: 66
<212> TYPE: PRT
<213> ORGANISM: Artificial Sequence
<220> FEATURE:
<223> OTHER INFORMATION: TraP17

<400> SEQUENCE: 3

Met Ala Gln Val Asn Asn Met Met Gln Gly Leu Arg Leu Ser Pro Ser
1               5                   10                  15

Asn Leu Ser Lys Pro Gln Thr Pro Leu Pro Ser His Ser Leu Leu Leu
                20                  25                  30

Gly Ser Asn Ser Leu Lys Asn Ser Val Ser Ala Ser Ser Val Ala Pro
            35                  40                  45

Ala Pro Ala Cys Ser Ala Pro Ala Gly Ala Gly Arg Arg Ala Val Val
        50                  55                  60

Val Arg
65

<210> SEQ ID NO 4

```
<211> LENGTH: 67
<212> TYPE: PRT
<213> ORGANISM: artificial sequence
<220> FEATURE:
<223> OTHER INFORMATION: TraP18

<400> SEQUENCE: 4

Met Ala Ala Thr Met Ala Ser Asn Ala Ala Ala Ala Ala Val Ser
 1               5                  10                  15

Leu Asp Gln Ala Val Ala Ala Ser Ala Ala Phe Ser Ser Lys Thr Leu
                20                  25                  30

Asn Phe Gly Ser Asn Leu Arg Ile Ser Pro Lys Phe Met Ser Leu Thr
            35                  40                  45

Asn Lys Arg Val Gly Gly Gln Ser Ser Ile Val Pro Lys Ile Gln Ala
        50                  55                  60

Ser Val Ala
65

<210> SEQ ID NO 5
<211> LENGTH: 67
<212> TYPE: PRT
<213> ORGANISM: Artificial Sequence
<220> FEATURE:
<223> OTHER INFORMATION: TraP19

<400> SEQUENCE: 5

Met Ala Gln Ala Thr Thr Ile Asn Asn Gly Val His Thr Gly Gln Leu
 1               5                  10                  15

His His Thr Leu Pro Lys Thr Gln Leu Pro Lys Ser Ser Lys Val Asn
                20                  25                  30

Asp Val Val Pro His Val Tyr Ser Ala Pro Leu Ser Val Ala Arg Arg
            35                  40                  45

Ser Cys Ser Lys Ser Ser Ile Arg Ser Thr Arg Arg Leu Gln Thr Thr
        50                  55                  60

Val Cys Ser
65

<210> SEQ ID NO 6
<211> LENGTH: 60
<212> TYPE: PRT
<213> ORGANISM: artificial sequence
<220> FEATURE:
<223> OTHER INFORMATION: TraP26

<400> SEQUENCE: 6

Met Ala Gln Val Ser Met Ile Pro Asn Ala Ile Gln Ala Pro Cys Ser
 1               5                  10                  15

Ile Ser Leu Ser Lys Ser Gln Ala Gly Lys Val Arg Lys Val Ser
                20                  25                  30

Leu Lys Pro Asn Gln His Ala Ala Trp Gly Leu Arg Arg Ser Gly Met
            35                  40                  45

Arg Val Gly Asn Pro Glu Val Val Val Ser Ala Ser
        50                  55                  60

<210> SEQ ID NO 7
<211> LENGTH: 61
<212> TYPE: PRT
<213> ORGANISM: artificial sequence
<220> FEATURE:
<223> OTHER INFORMATION: TraP27

<400> SEQUENCE: 7
```

Met Ala Thr Phe Thr Arg Val Cys His Thr Ala Arg Lys Ser Phe Val
1               5                   10                  15

Ser Leu Ser Asn Ser Gln Ala Asn Ser Pro Val Ser Val Arg Phe Leu
            20                  25                  30

Ser Leu Pro Met Pro Ala Ala Arg Pro Ala Val Lys Ser Gly Val Arg
        35                  40                  45

Leu Trp Gly Cys Arg Leu Ser Phe Lys Val Ser Ala Ser
    50                  55                  60

<210> SEQ ID NO 8
<211> LENGTH: 60
<212> TYPE: PRT
<213> ORGANISM: Artificial Sequence
<220> FEATURE:
<223> OTHER INFORMATION: TraP28

<400> SEQUENCE: 8

Met Ala Val Gln Ser Asn Met Ile Cys Ala Gly Val Ala Asn Pro Phe
1               5                   10                  15

Val Ser Pro Asn Leu Ser Lys Thr Arg Ala Ser Lys Ser Val Tyr Ser
            20                  25                  30

Val Leu Gly Thr Arg Leu Asn Ser Ser Ala Arg Gly Lys Lys Ser Ala
        35                  40                  45

Met Pro Leu Ile Gly Asn Arg Val Pro Val Ser Ala
    50                  55                  60

<210> SEQ ID NO 9
<211> LENGTH: 217
<212> TYPE: DNA
<213> ORGANISM: artificial sequence
<220> FEATURE:
<223> OTHER INFORMATION: TraP10 polynucleotide

<400> SEQUENCE: 9
atggctcaat cttctaggat ttgccacggt gttcaaaacc cttgcgtgat catctctaac      60
ctttccaagt ccaaccagaa caagtctcct ttcagcgttt ctcttagacc tagactttgg    120
ggagcttcta agtctaggat ccctatgcat aagaacggaa ccttcatggg aaacttcaat    180
gtgggaaagg gaaactctgg tgttttcaag gtttccg                             217

<210> SEQ ID NO 10
<211> LENGTH: 204
<212> TYPE: DNA
<213> ORGANISM: artificial sequence
<220> FEATURE:
<223> OTHER INFORMATION: TraP11 polynucleotide

<400> SEQUENCE: 10
atggctcaag tttctagggt tcacaacctt gctcagtcta ctcagatttt cggacactct      60
tccaactcta acaagctcaa gtctgttaac tctgtgtctc ttaagactca tcaacctagg    120
gcttcatctt ggggacttaa gaaatccgga accatgctta acggatctgt tatcaggcct    180
gttaaggtta ccgcttctgt gtct                                           204

<210> SEQ ID NO 11
<211> LENGTH: 198
<212> TYPE: DNA
<213> ORGANISM: artificial sequence
<220> FEATURE:
<223> OTHER INFORMATION: TraP17 polynucleotide -continued

<400> SEQUENCE: 11
atggctcaag ttaacaacat gatgcaaggg ttgagacttt caccctctaa cttgtccaaa    60
ccgcagactc cgctcccttc tcactctctg ctgcttggaa gcaatagcct caagaactct   120
gtctccgcat catccgttgc tccagctcct gcctgtagcg caccagctgg tgccggaagg   180
agggctgtgg tcgtgaga                                                 198

<210> SEQ ID NO 12
<211> LENGTH: 201
<212> TYPE: DNA
<213> ORGANISM: artificial sequence
<220> FEATURE:
<223> OTHER INFORMATION: TraP18 polynucleotide

<400> SEQUENCE: 12
atggctgcca ctatggcctc aaacgcagca gcagctgctg ctgtgagctt ggaccaagct    60
gttgccgcat ctgctgcctt cagtccaaa acacttaact ttggctccaa tctccgtatc   120
agcccaaagt ttatgagcct gactaacaag agagtgggtg acagtcatc tatagttcct   180 aagattcaag cctcagtcgc a                                             201

<210> SEQ ID NO 13
<211> LENGTH: 201
<212> TYPE: DNA
<213> ORGANISM: artificial sequence
<220> FEATURE:
<223> OTHER INFORMATION: TraP19 polynucleotide

<400> SEQUENCE: 13
atggcacaag ctacaacgat caacaatggt gtccacaccg acaactgca tcatacactt    60 ccaaagacgc agctcccgaa atcttctaag gtgaacgacg ttgtgcctca cgtctactcc   120
gctcccctta gcgttgcaag gaggtcatgc agcaaatcca gcataagatc cactagacgt   180
ctccagacca ctgtttgttc a                                             201

<210> SEQ ID NO 14
<211> LENGTH: 180
<212> TYPE: DNA
<213> ORGANISM: artificial sequence
<220> FEATURE:
<223> OTHER INFORMATION: TraP26 polynucleotide

<400> SEQUENCE: 14
atggcacaag tctccatgat acctaatgct attcaagcac cgtgctcaat ctccctgagc    60
aagtcccaag ctggaaagtc tgttcgcaag gtgtctctca aacctaatca gcacgcagct   120
tggggtttgc gtaggtctgg catgagggtg gggaacccag aggtggtcgt ttcagccagc   180

<210> SEQ ID NO 15
<211> LENGTH: 183
<212> TYPE: DNA
<213> ORGANISM: artificial sequence
<220> FEATURE:
<223> OTHER INFORMATION: TraP27 polynucleotide

<400> SEQUENCE: 15
atggctacgt ttaccagagt gtgccacaca gcaaggaaat ccttcgtttc actttcaaac    60
tctcaagcca attctcctgt gagcgttagg tttctgtcct tgcccatgcc agcagccaga   120
ccagctgtca agagcggagt gcgtctctgg ggttgtcgct tgtccttcaa ggtctcagct   180
tct                                                                 183

<210> SEQ ID NO 16
<211> LENGTH: 180
<212> TYPE: DNA
<213> ORGANISM: artificial sequence
<220> FEATURE:
<223> OTHER INFORMATION: TraP28 polynucleotide

<400> SEQUENCE: 16
atggcagtgc agtctaacat gatctgcgct ggtgtggcta acccgttcgt gtccccaaac 60
cttagcaaaa caagggcttc aaagtccgtc tacagcgttc tcgggactag actcaattca 120
tccgcaagag gcaagaagtc tgccatgcct ctgattggaa atcgtgttcc cgtctctgcc 180

<210> SEQ ID NO 17
<211> LENGTH: 9
<212> TYPE: DNA
<213> ORGANISM: artificial sequence
<220> FEATURE:
<223> OTHER INFORMATION: linker

<400> SEQUENCE: 17 gcttcttct 9

<210> SEQ ID NO 18
<211> LENGTH: 204
<212> TYPE: DNA
<213> ORGANISM: artificial sequence
<220> FEATURE:
<223> OTHER INFORMATION: Trap11 polynucleotide

<400> SEQUENCE: 18
atggctcaag tttctagggt tcacaacctt gctcagtcta ctcagatttt cggacactct 60
tccaactcta acaagctcaa gtctgttaac tctgtgagtc ttaagactca tcaaccgagg 120
gcttcatctt ggggacttaa gaaatccgga accatgctta acggatcagt tatcagacct 180
gtgaaagtta ccgcttctgt gtct 204

<210> SEQ ID NO 19
<211> LENGTH: 1902
<212> TYPE: DNA
<213> ORGANISM: Bacillus thuringiensis

<400> SEQUENCE: 19
atgaacaacg ttctcaactc tgggagaacc accatctgcg acgcgtacaa tgtggtggca 60
cacgacccat tctcatttga gcacaagagc ctggatacga tccagaaaga gtggatggaa 120
tggaaaagga cggaccattc cttgtacgtt gctccagtgg tgggcactgt gtcctcgttc 180
ctcctcaaga aagtggggtc gctgatcggg aagcggatac tctccgaact ctggggaatc 240
atctttccgt ctggctcaac aaacttgatg caagacatac tgagagagac tgagcagttc 300
ttgaatcaga ggctgaatac ggacacgctg gcgagggtga acgctgaact cattggcctc 360
caagcgaaca ttagagagtt caatcagcaa gttgataact ttctgaaccc cacacagaat 420
ccagtgcctc tgtccatcac atcatctgtg aacacaatgc agcagctgtt cttgaatagg 480
ctgccacagt ttcagattca aggctatcaa ctgcttcttc tgcctctgtt tgctcaagct 540
gcgaacatgc acctcagctt catcagagac gtgattctga acgcagatga gtggggaatc 600
agcgctgcca ctttgaggac ctacagagat tacttgagga actatacacg cgattactca 660
aactactgca tcaacaccta tcaaacagcg tttaggggac ttaacaccag actgcacgac 720

```
atgcttgagt tccggactta catgttcctc aacgtctttg agtatgtctc gatttggtcc   780
ctcttcaagt atcagagcct tatggtctcc tctggtgcta acctctacgc ctcgggttcc   840
ggaccgcagc agacccagtc attcactgcc agaactggc cattcctcta cagccttttc    900
caagtgaaca gcaactacat cttgtctggc atctctggca aaggctctc tatcacattt    960 ccgaacattg gtggcctgcc tggctccacg acgacacaca gcctcaattc cgcacgcgtc  1020
aactactcgg gtggggtctc ctccggactc attggtgcca ctaacttgaa ccataacttc  1080
aactgttcaa cggtgctgcc acccctttca actccgtttg tcagatcgtg gcttgattct  1140
ggcactgaca gagagggagt tgccacgagc accaactggc agaccgagtc cttccagacc  1200
acactttcgc tgcgctgcgg tgccttctca gcgaggggaa actcgaacta cttcccagac  1260
tacttcatac gcaacattag cggagtcccg ttggtgatcc ggaatgagga cctcaccaga  1320
cctcttcact acaatcagat acgcaacatc gaaagcccat ctgggacacc tggaggtgca  1380
agggcatact tggttagcgt tcacaaccgg aagaacaaca tctatgctgc taatgagaat  1440
gggaccatga ttcatcttgc accggaagat tacactggct tcacgatctc acccatccat  1500
gccacccaag tgaacaacca gactcgcacg ttcatctcag agaagttcgg caaccaaggt  1560
gacagcctcc gcttcgaaca gagcaacacc acagccagat acacccttag aggcaatggc  1620
aacagctaca atctctatct gagggtgtct agcattggca attcgaccat tcgggtgacg  1680
atcaatggtc gcgtttacac ggtctccaac gtcaatacga ccactaacaa tgatggggtc  1740
aatgacaatg gtgctcgctt ctccgacatc aacatcggca acatcgtcgc ttccgacaac  1800
accaatgtta cgctggacat caatgtcacc ttgaactctg gcacacccttt cgatctgatg  1860 aacatcatgt ttgtccccac caatcttcct cccctctact ga                      1902
```

<210> SEQ ID NO 20
<211> LENGTH: 69
<212> TYPE: PRT
<213> ORGANISM: Brassica napus

<400> SEQUENCE: 20

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
    50                  55                  60

Thr Ala Ser Val Ser
65

<210> SEQ ID NO 21
<211> LENGTH: 71
<212> TYPE: PRT
<213> ORGANISM: Glycine max

<400> SEQUENCE: 21

Met Ala Gln Val Ser Arg Val His Asn Leu Ala Gln Ser Thr Gln Ile
1               5                   10                  15

Phe Gly His Ser Ser Asn Ser Asn Lys Leu Lys Ser Val Asn Ser Val
            20                  25                  30

Ser Leu Arg Pro Arg Leu Trp Gly Ala Ser Lys Ser Arg Ile Pro Met
        35                  40                  45

His Lys Asn Gly Ser Phe Met Gly Asn Phe Asn Val Gly Lys Gly Asn
            50                  55                  60

Ser Gly Val Phe Lys Val Ser
 65                  70

<210> SEQ ID NO 22
<211> LENGTH: 65
<212> TYPE: PRT
<213> ORGANISM: Calystegia

<400> SEQUENCE: 22

Met Ala Gln Val Asn Asn Met Met Gln Gly Leu Arg Leu Ser Pro Ser
 1               5                  10                  15

Asn Leu Ser Lys Pro Gln Thr Pro Leu Pro Ser His Ser Leu Leu Leu
            20                  25                  30

Gly Ser Asn Ser Leu Lys Asn Ser Ser Val Ser Val Lys Phe Phe Lys
        35                  40                  45

Thr Gly Lys Asp Ser Ile Phe Thr Ala Ala Arg Ser Pro Leu Lys Val
    50                  55                  60

Arg
 65

<210> SEQ ID NO 23
<211> LENGTH: 61
<212> TYPE: PRT
<213> ORGANISM: Chlamydomonas reinhardtii

<400> SEQUENCE: 23

Met Gln Leu Leu Asn Gln Arg Gln Ala Leu Arg Leu Gly Arg Ser Ser
 1               5                  10                  15

Ala Ser Lys Asn Gln Gln Val Ala Pro Leu Ala Ser Arg Pro Ala Ser
            20                  25                  30

Ser Leu Ser Val Ser Ala Ser Ser Val Ala Pro Ala Pro Ala Cys Ser
        35                  40                  45

Ala Pro Ala Gly Ala Gly Arg Arg Ala Val Val Val Arg
    50                  55                  60

<210> SEQ ID NO 24
<211> LENGTH: 58
<212> TYPE: PRT
<213> ORGANISM: Oryza sativa

<400> SEQUENCE: 24

Met Ala Ala Thr Met Ala Ser Asn Ala Ala Ala Ala Ala Ala Val Ser
 1               5                  10                  15

Leu Asp Gln Ala Val Ala Ala Ser Ala Ala Phe Ser Ser Arg Lys Gln
            20                  25                  30

Leu Arg Leu Pro Ala Ala Ala Arg Gly Gly Met Arg Val Arg Val Arg
        35                  40                  45

Ala Arg Gly Arg Arg Glu Ala Val Val Val
    50                  55

<210> SEQ ID NO 25
<211> LENGTH: 67
<212> TYPE: PRT
<213> ORGANISM: Amaranthus

<400> SEQUENCE: 25

Met Ala Gln Ala Thr Thr Ile Asn Asn Gly Val His Thr Gly Gln Leu

```
               1               5                  10                 15
His His Thr Leu Pro Lys Thr Gln Leu Pro Lys Ser Ser Lys Thr Leu
              20                  25                 30

Asn Phe Gly Ser Asn Leu Arg Ile Ser Pro Lys Phe Met Ser Leu Thr
              35                  40                 45

Asn Lys Arg Val Gly Gly Gln Ser Ser Ile Val Pro Lys Ile Gln Ala
              50                  55                 60

Ser Val Ala
65

<210> SEQ ID NO 26
<211> LENGTH: 71
<212> TYPE: PRT
<213> ORGANISM: Dunaliella salina

<400> SEQUENCE: 26

Met Leu Ala Arg Gln Gly Gly Ser Leu Arg Ala Ser Gln Cys Asn Ala
1               5                  10                 15

Gly Leu Ala Arg Arg Val Glu Val Gly Ala Leu Val Val Pro Arg Pro
              20                  25                 30

Ile Ser Val Asn Asp Val Val Pro His Val Tyr Ser Ala Pro Leu Ser
              35                  40                 45

Val Ala Arg Arg Ser Cys Ser Lys Ser Ser Ile Arg Ser Thr Arg Arg
              50                  55                 60

Leu Gln Thr Thr Val Cys Ser
65                  70

<210> SEQ ID NO 27
<211> LENGTH: 1428
<212> TYPE: DNA
<213> ORGANISM: artificial sequence
<220> FEATURE:
<223> OTHER INFORMATION: Trap26 DGT28 fusion coding sequence

<400> SEQUENCE: 27
atggcacaag tctccatgat acctaatgct attcaagcac cgtgctcaat ctccctgagc    60
aagtcccaag ctggaaagtc tgttcgcaag gtgtctctca aacctaatca gcacgcagct   120
tggggtttgc gtaggtctgg catgagggtg gggaacccag aggtggtcgt ttcagccagc   180
gcaagaggga tgccagcctt gtctttacct ggatcaaaga gtatcacagc tagggcactc   240
tttcttgctg ctgctgctga tggggttact actttggtga ggccattgag aagtgacgac   300
acagaaggat tcgctgaggg gttagttcgt ttaggctatc gtgtagggag acacccgat    360 acttggcaag tcgatggcag accacaagga ccagcagtgg ctgaggctga cgtctactgt   420
agagacggag caaccaccgc tagattcttg ccaaccttag cagctgctgg tcacggaaca   480
tacagatttg atgcttcacc acagatgagg agacgtcctc ttttgccctt aagcagagcc   540
ttgagggatt tgggtgtcga tcttagacac gaagaagctg aaggtcatca ccctctgact   600
gtccgtgctg ctggggttga aggaggagag gttactttgg atgctggtca gtcaagtcag   660
tatctcactg ccttgttgct ccttggtccc cttacaagac aaggactgag gataagggtt   720
actgatttgg tgtcagcacc atacgtggag attacgcttg caatgatgag ggctttcgga   780
gttgaagtgg caagggaggg agatgtgttc gttgttccac tggtggata tcgtgcaact   840 acgtatgcta tagaacccga cgcaagtact gcttcttact tcttcgcagc tgctgctttg   900
actcctggag ctgaagtgac tgtacctggg ttaggcacgg agcacttca aggagatttg   960
```

```
ggatttgtag atgtcttaag gagaatggga gccgaggtgt ccgtaggagc tgatgcaacc   1020
actgttagag gaactggtga attgcgtggc cttacagcca acatgagaga cataagtgat   1080
acgatgccga ccctcgctgc aatagcaccc tttgctagtg ctccagttag aatcgaggat   1140
gttgccaaca ctcgtgtcaa agaatgtgac agacttgagg cttgtgcaga gaaccttagg   1200
aggttgggag taagggttgc aacgggtccg gactggattg agatacaccc tggtccagct   1260
actggtgctc aagtcacaag ctatggtgat cacagaattg tgatgtcatt tgcagtgact   1320
ggacttcgtg tgcctgggat cagcttcgac gaccctggct gtgttcgtaa gacttttcct   1380
gggtttcacg aggctttcgc agaattgagg cgtggcattg ggagctga              1428
```

<210> SEQ ID NO 28
<211> LENGTH: 1431
<212> TYPE: DNA
<213> ORGANISM: artificial sequence
<220> FEATURE:
<223> OTHER INFORMATION: Trap27 DGT28 fusion coding sequence

<400> SEQUENCE: 28

```
atggctacgt ttaccagagt gtgccacaca gcaaggaaat ccttcgtttc actttcaaac     60
tctcaagcca attctcctgt gagcgttagg tttctgtcct tgcccatgcc agcagccaga   120
ccagctgtca agagcggagt gcgtctctgg ggttgtcgct tgtccttcaa ggtctcagct   180
tctgcaagag ggatgccagc cttgtctttg cctggatcaa agagtatcac agctagggca   240
ctctttcttg ctgctgctgc tgatgggggtt actactttgg tgaggccatt gagaagtgac   300
gacacagaag gattcgctga gggggttagtt cgtttaggct atcgtgtagg gaggacaccc   360
gatacttggc aagtcgatgg cagaccacaa ggaccagcag tggctgaggc tgacgtctac   420
tgtagagacg gagcaaccac cgctagattc ttgccaaccct tagcagctgc tggtcacgga   480
acatacagat ttgatgcttc accacagatg aggagacgtc ctcttttgcc cttaagcaga   540
gccttgaggt atttgggtgt cgatcttaga cacgaagaag ctgaaggtca tcaccctctg   600
actgtccgtg ctgctggggt tgaaggagga gaggttactt tggatgctgg tcagtcaagt   660
cagtatctca ctgccttgtt gctccttggt ccccttacaa gacaaggact gaggataagg   720
gttactgatt tggtgtcagc accatacgtg agagattacgc ttgcaatgat gagggctttc   780
ggagttgaag tggcaaggga gggagatgtg ttcgttgttc cacctggtgg atatcgtgca   840
actacgtatg ctatagaacc cgacgcaagt actgcttctt acttcttcgc agctgctgct   900
ttgactcctg gagctgaagt gactgtacct gggttaggca cgggagcact tcaaggagat   960
ttgggatttg tagatgtctt aaggagaatg ggagccgagg tgtccgtagg agctgatgca   1020
accactgtta gaggaactgg tgaattgcgt ggccttacag ccaacatgag agacataagt   1080
gatacgatgc cgaccctcgc tgcaatagca ccctttgcta gtgctccagt tagaatcgag   1140
gatgttgcca cactcgtgt caaagaatgt gacagacttg aggcttgtgc agagaacctt   1200
aggaggttgg gagtaagggt tgcaacgggt ccggactgga ttgagataca ccctggtcca   1260
gctactggtg ctcaagtcac aagctatggt gatcacagaa ttgtgatgtc atttgcagtg   1320
actggacttc gtgtgcctgg gatcagcttc gacgaccctg gctgtgttcg taagactttt   1380
cctgggtttc acgaggcttt cgcagaattg aggcgtggca ttgggagctg a              1431
```

<210> SEQ ID NO 29
<211> LENGTH: 19
<212> TYPE: DNA
<213> ORGANISM: artificial sequence

```
<220> FEATURE:
<223> OTHER INFORMATION: primer

<400> SEQUENCE: 29
agccacatcc cagtaacga                                              19

<210> SEQ ID NO 30
<211> LENGTH: 17
<212> TYPE: DNA
<213> ORGANISM: artificial sequence
<220> FEATURE:
<223> OTHER INFORMATION: primer

<400> SEQUENCE: 30
cctccctctt tgacgcc                                                17

<210> SEQ ID NO 31
<211> LENGTH: 20
<212> TYPE: DNA
<213> ORGANISM: artificial sequence
<220> FEATURE:
<223> OTHER INFORMATION: primer

<400> SEQUENCE: 31
cagcccaatg aggcatcagc                                             20

<210> SEQ ID NO 32
<211> LENGTH: 20
<212> TYPE: DNA
<213> ORGANISM: artificial sequence
<220> FEATURE:
<223> OTHER INFORMATION: primer

<400> SEQUENCE: 32
cttcaccgcc ttagctttct                                             20

<210> SEQ ID NO 33
<211> LENGTH: 24
<212> TYPE: DNA
<213> ORGANISM: artificial sequence
<220> FEATURE:
<223> OTHER INFORMATION: primer

<400> SEQUENCE: 33
gtgaagaaga agctttgggt attg                                        24

<210> SEQ ID NO 34
<211> LENGTH: 24
<212> TYPE: DNA
<213> ORGANISM: artificial sequence
<220> FEATURE:
<223> OTHER INFORMATION: primer

<400> SEQUENCE: 34
cgtgacctag tcgtcctcgt cttt                                        24

<210> SEQ ID NO 35
<211> LENGTH: 25
<212> TYPE: DNA
<213> ORGANISM: artificial sequence
<220> FEATURE:
<223> OTHER INFORMATION: primer

<400> SEQUENCE: 35
agagaagttt cgacggattt cgggc                                       25
```

```
<210> SEQ ID NO 36
<211> LENGTH: 22
<212> TYPE: DNA
<213> ORGANISM: artificial sequence
<220> FEATURE:
<223> OTHER INFORMATION: primer

<400> SEQUENCE: 36
gaggattagg gtttcaacgg ag                                              22

<210> SEQ ID NO 37
<211> LENGTH: 21
<212> TYPE: DNA
<213> ORGANISM: artificial sequence
<220> FEATURE:
<223> OTHER INFORMATION: primer

<400> SEQUENCE: 37
gagaattgag ctgagacgag g                                               21
```